United States Patent
Gregerson

(10) Patent No.: US 12,361,631 B2
(45) Date of Patent: Jul. 15, 2025

(54) SYSTEM AND METHOD FOR GENERATION OF REGISTRATION TRANSFORM FOR SURGICAL NAVIGATION

(71) Applicant: See All AI Inc., Nashua, NH (US)

(72) Inventor: Eugene Alma Gregerson, North Salt Lake, UT (US)

(73) Assignee: See All AI Inc., Nashua, NH (US)

( * ) Notice: Subject to any disclaimer, the term of this patent is extended or adjusted under 35 U.S.C. 154(b) by 0 days.

(21) Appl. No.: 18/974,399

(22) Filed: Dec. 9, 2024

(65) Prior Publication Data

US 2025/0186130 A1 Jun. 12, 2025

Related U.S. Application Data

(60) Provisional application No. 63/607,956, filed on Dec. 8, 2023, provisional application No. 63/608,122, filed on Dec. 8, 2023.

(51) Int. Cl.
| | |
|---|---|
| *A61B 34/20* | (2016.01) |
| *A61B 6/00* | (2024.01) |
| *G06T 7/33* | (2017.01) |
| *G06T 7/73* | (2017.01) |

(Continued)

(52) U.S. Cl.
CPC ............... *A61B 34/20* (2016.02); *A61B 6/52* (2013.01); *G06T 7/33* (2017.01); *G06T 7/73* (2017.01); *G06T 11/006* (2013.01); *A61B 2034/2065* (2016.02); *A61B 2090/367* (2016.02);

(Continued)

(58) Field of Classification Search
CPC ............ A61B 34/20; A61B 2034/2065; A61B 2090/367; A61B 2090/376; A61B 6/52; G06T 7/33; G06T 7/73; G06T 11/006; G06T 2207/10116; G06T 2207/30204

See application file for complete search history.

(56) References Cited

U.S. PATENT DOCUMENTS

| | | |
|---|---|---|
| 10,258,414 B2 | 4/2019 | O'Grady et al. |
| 10,709,394 B2 | 7/2020 | Zhou et al. |
| 10,839,543 B2 | 11/2020 | Cheng et al. |

(Continued)

FOREIGN PATENT DOCUMENTS

WO 2023/186996 A1 10/2023

OTHER PUBLICATIONS

Jecklin et al., "Domain adaptation strategies for 3D reconstruction of the lumbar spine using real fluoroscopy data," Science Direct, Aug. 2024, https://doi.org/10.1016/j.media.2024.103322 (19 pgs.).

(Continued)

*Primary Examiner* — Amelie R Davis
(74) *Attorney, Agent, or Firm* — ArentFox Schiff LLP; Bruce D. Jobse

(57) ABSTRACT

A system and method combine optical and radiographic data to enhance imaging capabilities. Specifically, the system combines visually obtained patient pose position information and radiographic image information to facilitate calibrated surgical navigation. The process involves a data acquisition phase, a system calibration phase, a volume reconstruction phase, and a surgical navigation phase, all resulting in the alignment of instrument coordinates with the patient and reconstructed volume coordinates enabling tracking and navigation of surgical instruments within a reconstructed 3D volume of the patient anatomy, even if such anatomy is not exposed during a procedure.

1 Claim, 21 Drawing Sheets

(51) Int. Cl.
*G06T 11/00* (2006.01)
*A61B 90/00* (2016.01)

(52) U.S. Cl.
CPC ............... *A61B 2090/376* (2016.02); *G06T 2207/10116* (2013.01); *G06T 2207/30204* (2013.01)

(56) References Cited

U.S. PATENT DOCUMENTS

| | | | |
|---|---|---|---|
| 11,207,135 | B2 | 12/2021 | Schmidt et al. |
| 11,379,985 | B2 | 7/2022 | Wang et al. |
| 2005/0159759 | A1 | 7/2005 | Harbaugh et al. |
| 2008/0285843 | A1 | 11/2008 | Lim |
| 2010/0249800 | A1 | 9/2010 | Kim et al. |
| 2013/0170627 | A1 | 7/2013 | Topfer et al. |
| 2017/0156800 | A1 | 6/2017 | Brown |
| 2018/0315221 | A1 | 11/2018 | Jones et al. |
| 2018/0315243 | A1 | 11/2018 | Mahler et al. |
| 2019/0216409 | A1 | 7/2019 | Zhou et al. |
| 2020/0222018 | A1 | 7/2020 | Van Walsum et al. |
| 2021/0113176 | A1 | 4/2021 | Sehnert et al. |
| 2021/0169504 | A1 | 6/2021 | Brown |
| 2021/0192810 | A1 | 6/2021 | Paysan et al. |
| 2022/0020215 | A1 | 1/2022 | Banerjee et al. |
| 2022/0031423 | A1 | 2/2022 | Halpert |
| 2024/0185509 | A1 | 6/2024 | Kovler et al. |

OTHER PUBLICATIONS

Jecklin et al., "X23D—Intraoperative 3D Lumbar Spine Shape Reconstruction Based on Sparse Multi-View X-ray Data," Journal of Imaging, Oct. 2022, doi.org/10.3390/jimaging8100271 (17 pgs.).

Invitation to Pay Additional Fees received for PCT Patent Application No. PCT/US2024/059213, mailed on Jan. 2, 2025, 2 pages.

Invitation to Pay Additional Fees received for PCT Patent Application No. PCT/US2024/059215, mailed on Jan. 30, 2025, 2 pages.

Invitation to Pay Additional Fees received for PCT Patent Application No. PCT/US2024/059236, mailed on Jan. 29, 2025, 2 pages.

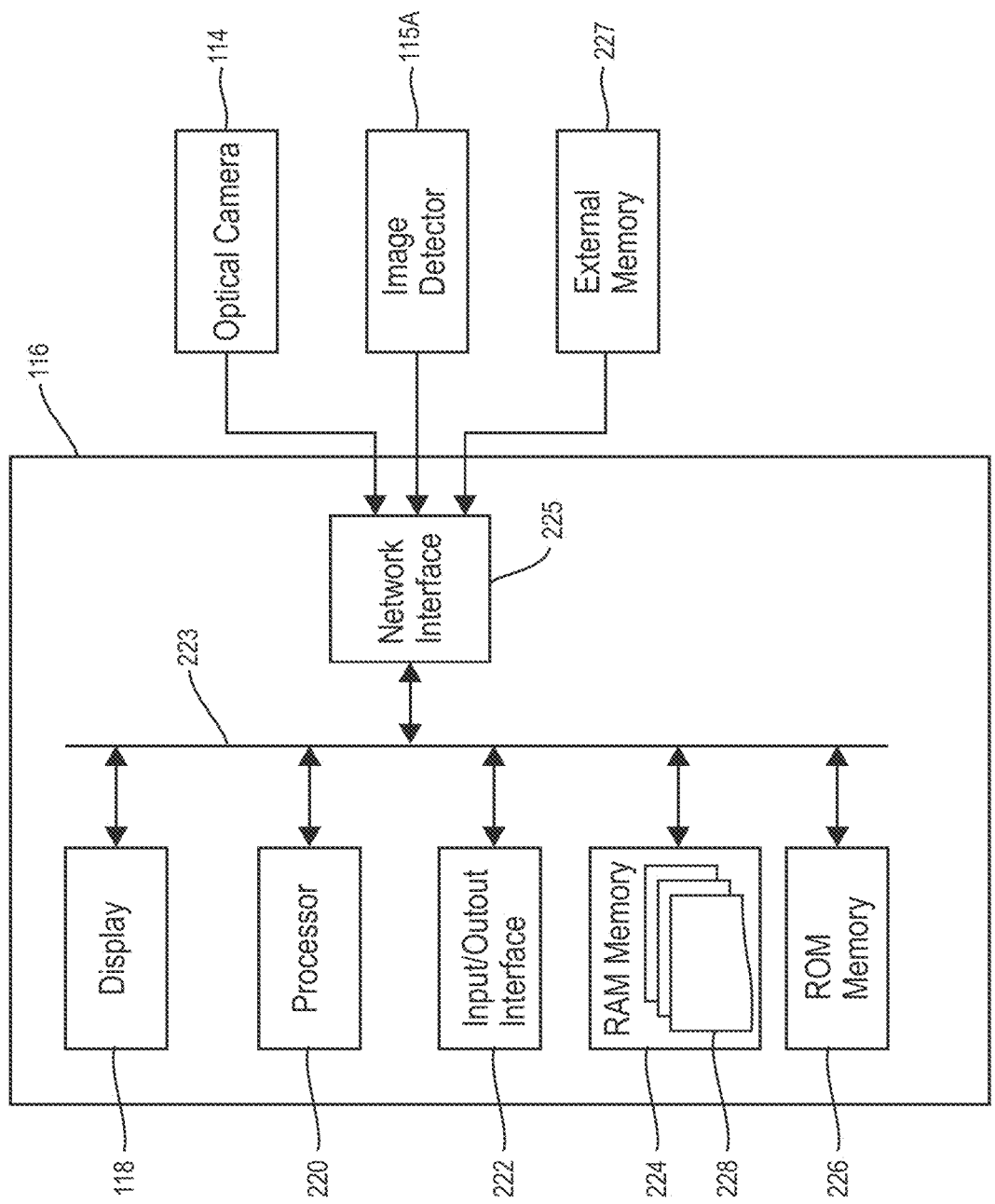

SYSTEM AND METHOD FOR GENERATION OF REGISTRATION TRANSFORM FOR SURGICAL NAVIGATION

CROSS REFERENCE TO RELATED APPLICATIONS

This application claims the benefit of priority to the following applications, filed by the same Applicant, See All AI Inc., the entire contents of all of which are incorporated herein by this reference for all purposes:
U.S. Provisional Application No. 63/607,956, filed on Dec. 8, 2023, and,
U.S. Provisional Application No. 63/608,122, filed on Dec. 8, 2023.
Further, the entire contents of the following applications, filed by the same Applicant on an even date herewith, are incorporated herein by this reference for all purposes:
U.S. patent application Ser. No. 18/974,545, entitled "System and Method for Reconstruction of 3D Volumes from Biplanar X-ray Images"; and
U.S. patent application Ser. No. 18/974,359, entitled "Wire-Based Calibration Apparatus for X-ray Imaging Systems".

FIELD OF THE INVENTION

Disclosed is a system and technique related to three-dimensional (3D) imaging in medical diagnostics for providing surgical navigation, and, more particularly to tracking of surgical instruments within a reconstructed 3D volume, and aligning the instrument coordinates with the patient and volume coordinate systems.

BACKGROUND OF THE INVENTION

Traditional static radiographic images, including X-rays and computer tomography, have been used in medical imaging and diagnostics, however, these technologies are not well suited for procedures requiring real time imaging of patient anatomy and/or surgical navigation assistance. Instead, fluoroscopy, comprising pulsed radiographic energy, is utilized for multiple procedures in which real time visual assistance is required during the procedure. However, fluoroscopic images provide only two-dimensional views of the patient anatomy and are not suitable for complicated procedures, especially surgical procedures which require three-dimensional image of the patient anatomy and real time displays of instruments relative to the patient's anatomy. Unfortunately, real time generation of a patient's anatomy via computerized tomography is very expensive. More recently, attempts have been made to generate or reconstruct three-dimensional volume of CT quality images from a limited number of X-rays, as disclosed in U.S. Pat. No. 10,709,394, however, the disclosed system and method is not useful for real time surgical navigation assistance and the resulting volume from lack of accuracy due to the averaging of values to create the reconstructed CT images. Accordingly, a need exists for a way to provide three-dimensional CT quality images in real-time to assist with surgical navigation.

Computer assisted surgical systems utilize predominantly visual position data to assist surgeons, without the benefit of radiographic images, such as that disclosed in US Patent Application Publication US20050159759A1, however, such systems are typically limited to used identifying proper incision location and surgical navigation guidance relative to only exposed patient anatomy. Accordingly, a further need exists for a way to provide real-time three-dimensional CT quality images of unexposed patient anatomy to assist with surgical navigation.

Attempts have been made to utilize both radiographic images and visually acquired positional data to assist with surgical navigation, such as that disclosed in US Patent Application Publication US20210169504A1, however, such system is not capable of creating a three-dimensional volume of CT quality images useful for real time surgical navigation purposes. The difficulty in attempting to utilize visually acquired position information and radiographic images is the calibration of the camera's coordinate system with that of the X-ray imaging system. This problem is further compounded when trying to align the position of a surgical instrument as defined within the coordinate system of the patient or camera within the coordinate system of a three dimensional volume of radiographic images, such as CT images.

Accordingly, a need exists for a system and method which is capable of accurately creating a 3D volume of the patient anatomy in an efficient, near real-time manner from relatively few radio graphic images and which is further capable of aligning the detected position of a surgical instrument in the patient coordinate space with the created three dimensional volume of CT quality images of the patients anatomy, to facilitate accurate navigational guidance of instruments relative to both exposed and non-exposed patient anatomy.

As noted, medical imaging technologies, including fluoroscopic imaging are widely used in medical diagnostics and interventional procedures to obtain real-time images of the internal structures of a patient. Traditional fluoroscopic systems, however, do not automatically record detailed data on the position and orientation of each image with respect to the patient and the imaging device. This limitation can hinder the accurate reconstruction of three-dimensional volumes from the fluoroscopic images, needed for advanced diagnostic and therapeutic applications. This problem is relevant to surgical procedure involving the spine. The human spine comprises multiple bony vertebral bodies that can move relative to one another. Tracking each vertebral body during a spinal surgical procedure would be cumbersome, computationally intensive and time-consuming.

Intraoperative imaging plays a pivotal role in modern surgical navigation, enabling surgeons to make informed decisions based on real-time anatomical information. Traditional computed tomography (CT) scanners, while providing detailed 3D images, are often impractical in an operating room due to their size, cost, and the time required for scanning. A need exists for portable imaging solutions that can provide high-quality 3D reconstructions with minimal equipment and radiation exposure.

The challenge lies in reconstructing a 3D volume from limited two-dimensional (2D) projection data. The limited-angle problem in tomography states that accurate reconstruction is fundamentally challenging when projection data is insufficient or confined to a restricted angular range. This limitation poses significant hurdles in scenarios where acquiring multiple projections is impractical. Accordingly, a need exists for a system and technique for accurate reconstruction of a 3D volume from limited 2D projection data.

Moreover, precise tracking of surgical instruments relative to the patient's anatomy is essential for accurate navigation during surgery. Automatic registration of the surgical instruments to the patient coordinates and volume is needed, especially for minimally invasive procedures where the patient's anatomy does not need to be exposed for registration. This capability would enhance the practicality and safety of such procedures by reducing operative time and patient trauma.

Accordingly, a further need exists for a system and technique for automatic registration of surgical instruments to the patient coordinate system and 3D volume coordinate system to enable precise tracking of surgical instruments relative to the patient's anatomy.

SUMMARY OF THE INVENTION

Disclosed is a system and methods for combining optical and radiographic data to enhance imaging capabilities. Specifically, the disclosed system and method combine both visually obtained patient pose position information and radiographic image information to facilitate calibrated surgical navigation. The process involves a data acquisition phase, a system calibration phase, a volume reconstruction phase, and a surgical navigation phase, all resulting in the alignment of instrument coordinates with the patient and reconstructed volume coordinates enabling tracking and navigation of surgical instruments within a reconstructed 3D volume of a patient anatomy, even if the such anatomy is not exposed during a procedure.

Disclosed is a system and technique of 3D imaging and medical diagnostics for providing surgical navigation, and, more particularly to tracking of surgical instruments within a reconstructed 3D volume, and aligning the systems. The disclosed system and method combine precise pose estimation via camera calibration with deep learning techniques to reconstruct 3D volumes from only two biplanar X-ray images. The system further computes a registration transform that allows tracking of surgical instruments within the reconstructed volume, and aligning the instrument coordinates with the patient and volume coordinate systems. Importantly, the same registration transform is used to define the center and orientation of the voxel grid for back projection, ensuring consistency between the navigation and imaging components of the system.

One aspect of the disclosure is the automatic registration of surgical instruments surgical navigation. By enabling automatic registration, the system facilitates minimally invasive procedures where the patient's anatomy does not need to be exposed for registration purposes. Furthermore, the surgical instrument does not need a reference array. Tracking may be done by object recognition of the surgical instrument by the optical cameras and employing 3D localization algorithms to determine the instruments' poses relative to the patient reference marker.

An additional significant contribution is the correction of non-linear distortions in the X-ray images. The markers in the calibration target attached to the C-arm are utilized not only for pose estimation but also to determine non-linear distortions typically caused by X-ray image intensifier systems, such as pincushion and S-distortions. Accounting for these distortions is essential when back projecting the voxel grid onto the 2D X-ray images.

The grid used in the reconstruction is centered at the computed point of intersection of the X-ray projection vectors and aligned along basis vectors derived from these vectors, ensuring that the volume is in the patient's coordinate frame. Each voxel coordinate is projected onto the biplanar images using the calibration matrices, establishing a direct connection between the generalized Radon transform and the reconstructed volume. An additional motivation for centering the grid at the point of intersection and aligning it with the basis vectors is to ensure that when projected onto the two X-ray images, the grid points will generally fall within the field of view of the X-ray images. If the grid is not centered appropriately and oriented with the basis vectors, the projected grid points may fall outside the biplanar X-ray fields of view, rendering the volume less useful when passing the concatenated back projected volumes through the trained U-Net.

Disclosed is a registration transform process that allows for the precise alignment of a reconstructed 3D volume with the patient's actual anatomy, ensuring that surgical tools and procedures can be accurately guided based on the reconstructed images. The ability to generate this registration transform directly from the radiographic images used for 3D volume reconstruction streamlines the process, making it more efficient and reducing the need for additional imaging or calibration steps typically required in surgical navigation.

The disclosed system can be integrated into existing surgical navigation systems, enhancing accuracy and reliability. By providing a direct method to obtain a transformation matrix, e.g. 4×4, that encompasses both positional and rotational information, the system significantly aids in the precise orientation of surgical instruments and navigation within the surgical field.

In accordance with another aspect of the disclosure, a system and technique is disclosed for generation of a registration transform for surgical navigation by leveraging the central rays of the X-ray images. The central ray, defined as the ray that extends from the X-ray source to the detector, plays a pivotal role in this process. The disclosed technique is a shelf grounded in the geometric properties of the central rays and their interactions within the 3D volume. The method addresses key challenges in traditional calibration approaches, offering improved accuracy, robustness, and integration with 3D reconstruction workflows.

Disclosed is an imaging system that reconstructs three-dimensional (3D) computed tomography (CT) volumes from two biplanar X-ray images captured using a mobile X-ray C-arm equipped with optical tracking. The system utilizes an external optical camera to detect reference markers attached to both the patient and a calibration target mounted on the X-ray C-arm. The calibration target contains radiopaque markers with known spatial coordinates, visible in the X-ray images. During each X-ray capture, the optical camera records the six degrees of freedom (6-DoF) poses (rotation and translation) of the reference markers. The X-ray images are processed to detect the calibration markers, which are then used in a camera calibration algorithm to compute the intrinsic and extrinsic parameters of the X-ray system. These parameters provide the precise poses of the two independent X-ray projections, serving as inputs to a deep learning algorithm that reconstructs 3D CT volumes from the biplanar X-rays using the generalized Radon transform and a trained 3D U-Net.

Further disclosed is a method for tracking surgical instruments within the reconstructed volume by computing a registration transform that aligns the instrument coordinates with the patient and volume coordinate systems. The registration transform is also used to define the center and orientation of the voxel grid for back projection and reconstruction, ensuring consistency between the navigation and imaging components of the system. Automatic registration of the surgical instruments is a needed aspect of surgical navigation, especially in minimally invasive procedures where the patient's anatomy does not need to be exposed for registration. This capability enhances the practicality and safety of such procedures. Additionally, the surgical instruments may or may not require a reference array; one tracking approach utilizes object recognition by the optical cameras and 3D localization algorithms to determine the instruments' poses relative to the patient reference marker.

One aspect of the disclosed technique is the correction of non-linear distortions in the X-ray images. The radiopaque markers in the calibration target attached to the C-arm are also used to determine non-linear distortions typically caused by X-ray image intensifier systems, such as pincushion and S-distortions. Accounting for these distortions is essential when back projecting the voxel grid onto the 2D X-ray images. This step may not be necessary for flat panel X-ray detectors, which generally do not exhibit these types of distortions.

The reconstruction process is centered at the point of intersection of the X-ray projection vectors, and the volume is aligned along basis vectors derived from these vectors, ensuring that the voxel grid is defined in the patient's coordinate system. Each voxel coordinate is projected onto the biplanar images using the calibration matrices, connecting the generalized Radon transform to the reconstructed volume. This integration allows for precise instrument navigation within the patient's anatomy using the generated registration transform. An additional motivation for centering the grid at the point of intersection and aligning it with the basis vectors is to ensure that when projected onto the two X-ray images, the grid points will generally fall within the field of view of the X-ray images. If the grid is not centered appropriately and oriented with the basis vectors, the projected grid points may fall outside the biplanar X-ray fields of view, rendering the volume less useful when passing the concatenated back projected volumes through the trained U-Net. Disclosed is an in-depth mathematical description of the system components, marker detection, camera calibration, CT reconstruction, and instrument tracking processes, highlighting the motivations and challenges addressed in each section.

The calibration of X-ray images is a two-fold process involving both intrinsic and extrinsic parameters. Intrinsic calibration focuses on the internal characteristics of the X-ray imager, such as the lens distortions, focal length, and principal point.

Extrinsic calibration, on the other hand, deals with the spatial positioning and orientation of the X-ray imaging device. Extrinsic calibration involves determining the relative 3D poses of the X-ray images. This is accomplished either through encoders integrated within the X-ray imaging system or via an external navigation system. The external system records the precise pose positions of the imaging device during the image capture process. These pose positions are then used to accurately back-project the encoded images into the common coordinate system.

The combination of intrinsic and extrinsic calibrations ensures that each X-ray image is precisely aligned in terms of both its internal geometry and its spatial orientation. This dual calibration approach is essential for accurate back-projection and reconstruction of the 3D volume. It addresses and overcomes the traditional challenges faced in 3D imaging, particularly in scenarios where only a limited number of images and a restricted range of angles are available. The resulting 3D volume is not only complete but also exhibits high resolution and accuracy, marking a significant improvement over conventional methods.

The system uses a model capable of accurately reconstructing 3D volumes from a limited set of X-ray images. This model is achieved through a detailed and comprehensive training regime, enabling the accurate reconstruction of 3D volumes from X-ray images. The model training involves a sophisticated interplay between encoding X-rays, back-projecting them into a 3D volume, decoding this volume, and refining the system through iterative learning.

According to still another aspect of the disclosure, a method for generating a registration transform for surgical navigation systems, comprises: a) capturing a set of at least two radiographic images and generating, for each of the respective images, a central ray representing a path from a radiation source to a radiographic image detector; b) identifying an intersection point of the central rays; c) generating a registration transform based on the intersection point and orientation of the central rays and generating a 3D volume reconstruction from the at least two radiographic images, and d) integrating the registration transform with a surgical navigation system to align surgical tools with the reconstructed 3D volume. In embodiments c) comprises generating the registration transform as part of a process of generating a 3D volume reconstruction from the radiographic images. In embodiments, the registration transform includes positional information (x, y, z) and rotational information (yaw, pitch, roll) relative to a reference marker on one of a subject or the radiographic image detector.

According to yet another aspect of the disclosure, a system for surgical navigation, comprises: a) an image processing module for reconstructing a 3D volume from at least X-ray images and for identifying an intersection point of computed central rays of each of the X-ray images; b) a transform generation module for creating a registration transform based on the intersection point and orientation of the central rays each of the X-ray images, wherein the registration transform defines the positional and rotational relationship of a 3D volume relative to a physical reference marker on a subject; and c) a navigation interface utilizing the registration transform to visually align surgical instruments with the 3D volume. In embodiments, the system further comprises a physical reference marker on a subject.

According to still yet another aspect of the disclosure, a non-transitory computer-readable medium storing instructions that, when executed by a processor, cause a system to perform the method comprising: a) capturing a set of at least two radiographic images and generating, for each of the respective images, a central ray representing a path from a radiation source to a radiographic image detector; b) identifying an intersection point of the central rays; c) generating a registration transform based on the intersection point and orientation of the central rays and generating a 3D volume reconstruction from the at least two radiographic images, and d) integrating the registration transform with a surgical navigation system to align surgical tools with the reconstructed 3D volume. In embodiments c) comprises generating the registration transform as part of a process of generating a 3D volume reconstruction from the radiographic images. In embodiments, the registration transform includes positional information (x, y, z) and rotational information (yaw, pitch, roll) relative to a reference marker on one of a subject or the radiographic image detector.

According to a further aspect of the disclosure, a method for tracking surgical instruments comprises: A) detecting a position of an instrument in a subject coordinate system; B) constructing a registration transform defining a center and orientation of a voxel grid usable for back projection and reconstruction of a 3D volume; C) reconstructing a 3D volume from two biplanar images of the subject using the registration transform; and D) aligning the position of the instrument in the subject coordinate system with the reconstructed 3D volume. In embodiment, the method further comprises:

E) overlaying the aligned instrument position onto the reconstructed 3D volume. In embodiment, the registration transform includes positional (x, y, z) and rotational (yaw, pitch, roll) data relative to reference marker in the subject coordinate system.

According to still a further aspect of the disclosure, a method for marker-less surgical instrument tracking comprises: A) detecting a position of an instrument in a subject coordinate system using object recognition; and B) aligning coordinates of the instrument position with the subject coordinate system and coordinates of a volume, wherein aligning coordinates of the instrument position with the subject coordinate system and coordinates of a volume is done without a reference array associated with the instrument.

According to still a further aspect of the disclosure, a method of synchronizing coordinate systems in a surgical navigation system comprises: A) detecting a pose of a subject in a subject coordinate system; B) generating reconstructed 3D volume from two biplanar X-ray images of the subject pose; C) detecting a position of a instrument in the subject coordinate system; D) aligning the position of the instrument with the reconstructed volume through use of a shared registration transform; and E) overlaying the translated instrument position onto the reconstructed 3D volume.

According to yet a further aspect of the disclosure, a method of synchronizing coordinate systems in a surgical navigation system comprising: A) detecting pose information of a subject in a subject coordinate system; B) generating reconstructed 3D volume from at least two biplanar radiographic images of the subject pose; C) detecting pose information of a surgical instrument in the subject coordinate system; and D) aligning a position of the surgical instrument within the reconstructed volume through use of a generated shared registration transform. In embodiments, the method further comprises: E) overlaying the aligned instrument position onto the reconstructed 3D volume. In embodiments, the shared registration transform comprises both positional and rotational information and is at least partially derived from both the pose information. In embodiments, the shared registration transform is at least partially derived from both the pose information and the at least two biplanar radiographic images.

According to still a further aspect of the disclosure, a method of synchronizing coordinate systems in a surgical navigation system comprises: A) acquiring a pair of biplanar images; B) generating a projection vector from each of the biplanar images; C) deriving a registration transform function from parameters of the projection vectors; D) defining point of intersection of the projection vectors in a first three-dimensional space as a center of a voxel grid; E) back-projecting the voxel grid to create a three-dimensional volume of the biplanar images; F) detecting a position of an instrument within a patient coordinate system; G) aligning the instrument position with the three-dimensional volume; and H) projecting an image of the aligned instrument position overlayed over the three-dimensional volume.

BRIEF DESCRIPTION OF THE DRAWINGS

The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. Furthermore, elements may not be drawn to scale.

FIG. 17 is a conceptual illustration of a computer system suitable for use with the disclosed system and methods.

DETAILED DESCRIPTION

Disclosed is a system and methods for combining optical and radiographic data to enhance imaging capabilities. Specifically, the disclosed system and method combine both visually obtained patient pose position information and radiographic image information to facilitate calibrated surgical navigation. The process involves a data acquisition phase, a system calibration phase, a volume reconstruction phase, and a surgical navigation phase, all resulting in the alignment of instrument coordinates with the patient and reconstructed volume coordinates enabling tracking and navigation of surgical instruments within a reconstructed 3D volume of a patient anatomy, even if the such anatomy is not exposed during a procedure.

Figure 1:
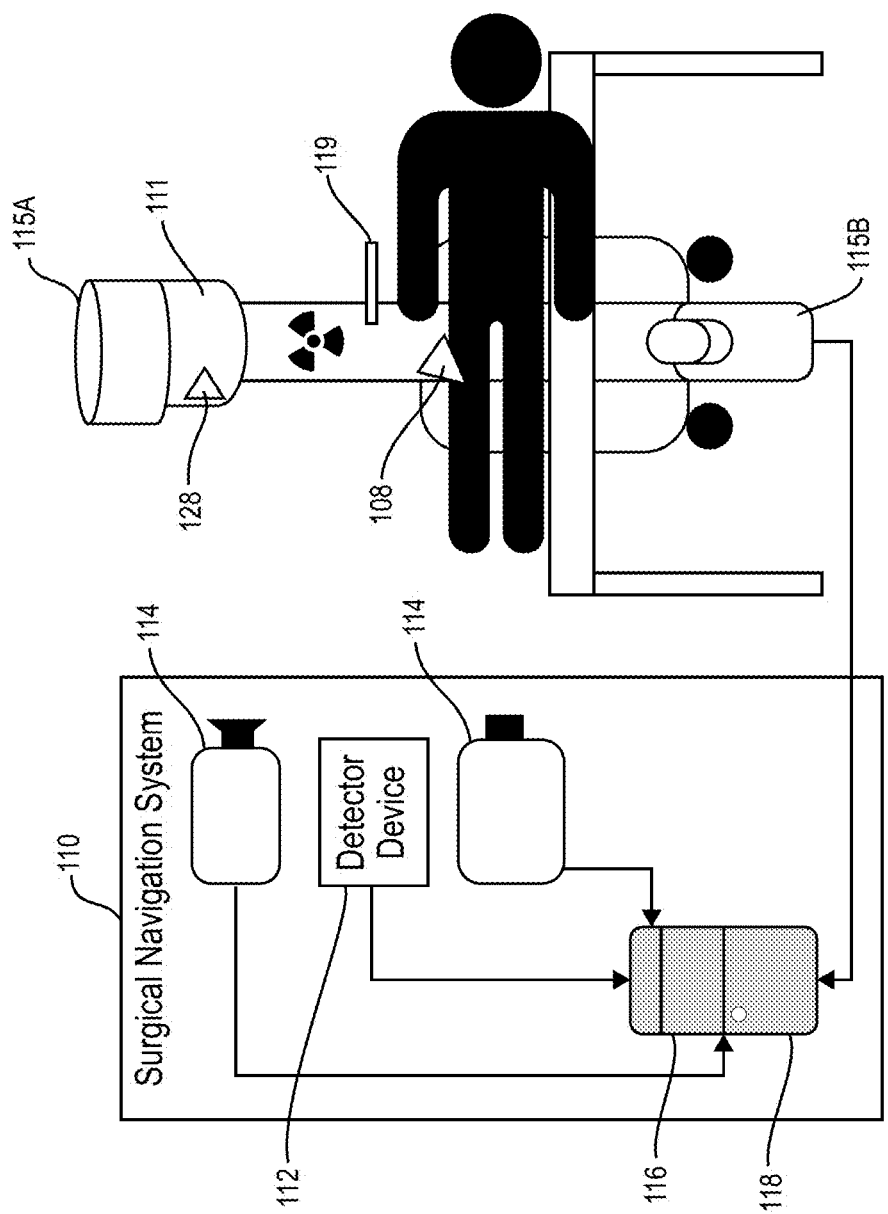
FIG. 1 is a conceptual illustration of a surgical navigation system in accordance with the disclosure.

FIG. 1 illustrates conceptually a surgical navigation system 110 suitable for use with the reference markers and anchors described herein. The surgical navigation system 110 may be used with a traditional fluoroscopy machine, e.g. a C-arm, having a source of radiation 115B disposed beneath the patient and a radiographic image detector 115A disposed on the opposite side of the patient.

In embodiments, surgical navigation system 110 comprises reference markers 108 or 128, a radiation detector 112, a calibration target 111, cameras 114, computer 116, and a display interface 118 used with an radiation source 115B and radiographic image detector 115A, device 115A. In embodiments, the components of surgical navigation system 110 may be contained within a single housing which is easily positionable along three axes within the surgical procedure space. Alternatively, one or more the components of surgical navigation system 110 may be located remotely from other components but interoperable therewith through suitable network infrastructure. The surgical system 110, and particularly cameras 114, track the reference marker 108 or 128 within the camera coordinate system, e.g. the patient coordinate system, and forward the positional information of the reference markers onto computer 116 for further processing.

One or more external optical camera 114 may be positioned to capture the operating area, as illustrated, and detect optical reference marker 8 attached to the patient and the reference marker 128 attached to the calibration target 111. External optical camera 14 provides real-time tracking of the 6-DoF poses (rotation and translation) of the markers 108 and 128. In embodiments, camera 114 may be implemented using one or more visible light cameras to capture real-time images of the surgical field including the patient and X-ray imaging system, e.g. a fluoroscope. A camera suitable for use as camera 114 is the Polaris product line of optical navigation products, commercially available from Northern Digital, Waterloo, Ontario, Canada. External camera 114 may be in communication with one or both of synchronizing device 112 and a processing unit 116. When the imaging systems X-ray is triggered, synchronizing device 112 identifies X-ray emissions relative to a predefined threshold level and signals computer 116 and/or external camera 114 and to capture pose information of the patient and imaging system itself via reference markers 108 and 128, respectively.

Reference markers 108 and 128 are fiducial markers that are easily detectable by the optical camera 114 and are attached to the patient and the calibration target 111, respectively, and serve as points of reference for coordinate transformations. The implementation of reference markers 108 and 128 is set forth in greater detail in co-pending U.S. patent application Ser. No. 18/974,434, entitled "Omni-View Unique Tracking Marker".

Figure 8:
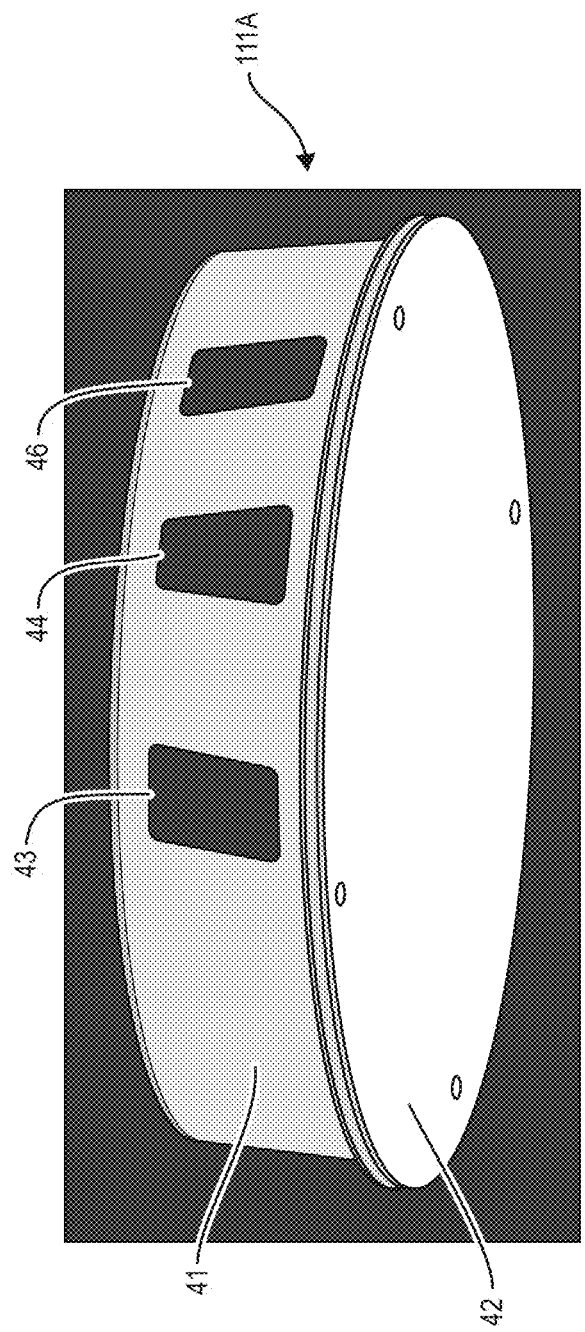
FIG. 8 is a conceptual perspective illustration of a calibration target apparatus in accordance with an illustrative embodiment.

Calibration target 111A, attachable to the radiographic image detector 115A, may be implemented with radiopaque wire markers embedded within the calibration target, as further described herein and in co-pending U.S. patent application Ser. No. 18/974,359, entitled "Wire-Based Calibration Apparatus for X-ray Imaging Systems". In embodiments, the calibration target may have the exterior body configuration of target 111A of FIG. 8A. Calibration target 111A comprises a target body 41 having a substantially circular shape which is attachable directly to the radiation detector housing of an imaging system. A cover 42 is attached to target body 41 and made of a material that is essentially transparent to radiation incident thereon so as not to block such radiation from reaching the radiation detector. In embodiments, multiple reference elements 43, 44 and 46 are attached to or embedded into a sidewall or surface of target body 41. Each of elements 43, 44 and 46 may have a similar or different shape relative to the other of the elements, but each element 43, 44 and 46 has a unique position relative to the target body 41. In this manner, when viewed by a color or visible light camera, the unique geometry and surface texture of markers 43, 44, and 46 enables the target 111A to be easily distinguished from its surroundings, regardless of a camera angle(s), to enable precise tracking of the position and orientation of target 111A and the radiation detector 115B in a three-dimensional space.

Figure 9:
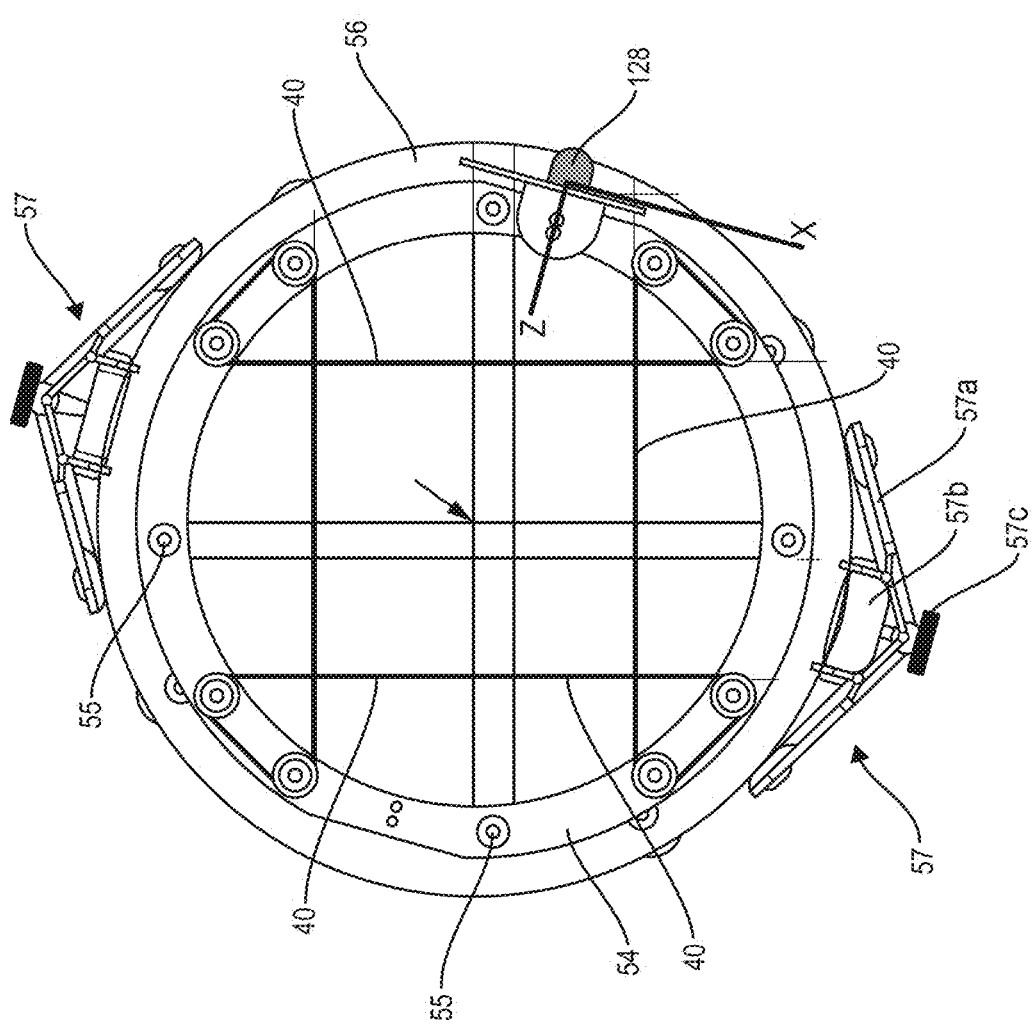
FIG. 9 is a top view illustration of a calibration target apparatus in accordance with an illustrative embodiment.

FIG. 9 is a top view illustration of a calibration target comprising a target body 52, a mounting mechanism 57, and a plurality of linear calibration markers 40 arranged in a known geometric pattern. Target body 52 comprises a pair of ring-shaped frames 54 and 56 coupled together but spaced apart by posts 55. A plurality of pads or suction cups (not shown) are disposed on the side of ring 56 which will be positioned adjacent a radiation detector to help secure the calibration target 111A thereagainst.

The mounting mechanism 57 comprises a pair of brackets are attached to opposing sides of frames 56, each with an clamping block 18 and tightening screw 59 to allow manual tightening of brackets 17a-b to the radiation detector. In this manner, mounting mechanism 57 facilitate removably securing calibration target 111A to the radiation detector of an imaging system.

In embodiments, target body 52 may be made from a substantially rigid or semirigid material and may have a circular exterior shape, as illustrated, for attachment to the radiation detector of a C-arm X-ray machine, or, may have other shapes adapted to be secured within the path of radiation incident on the radiation detector of an imaging system.

In embodiments, calibration markers 40 may be implemented with wires that may be made of all or partially radiopaque material (e.g., tungsten or steel) to ensure visibility in X-ray images. The wires 40 may be arranged at different known depths relative to the plane or face of the radiation detector to provide 3D spatial information. In embodiments, the wires may be positioned such that they are generally parallel to the face of the radiation detector, simplifying the projection geometry. In embodiments, the diameter of the wires is optimized to be large enough to be visible in the detected radiation images but small enough to occupy minimal pixel area to facilitate digital subtraction.

In embodiments, wires 40 may be implemented with Tungsten wires with diameter 0.5 mm, although other diameters may be used. In embodiments, wires 40 may be implemented with round wound or flat wound wires. Wires 40 may be placed at depths between $z=0$ mm and $z=-50$ mm relative to the calibration target origin. Wires 40 may be arranged in a grid pattern with known spacing, intersecting at known crossover points, as illustrated, although other intersecting wire patterns may be used.

The wires 40, as illustrated in FIG. 9 have known 3D spatial coordinates relative to reference marker 128 or reference elements 43, 44, and 46 attached to the calibration target 111A. Such wires are visible in the captured radiographic images 5 and 15 and used for calibrating the radiographic imaging system, including intrinsic correction of non-linear distortions. With of calibration target 111A and 111B, illustrated herein, there is no need for second reference marker 128, as previously described, to determine the position of the imaging system to which the calibration target is attached, since the reference elements 43, 44, and 46 collectively are detectable from the exterior of calibration target 111A.

Surgical Instrument(s) 119 may be equipped with optical markers or tracked using object recognition and 3D localization algorithms, as described further herein, and allow for real-time tracking and alignment within a 3D volume of CT quality images reconstruct from two radiographic image, e.g. X-rays.

Display interface 118 is operably coupled to computer 116 and provides real-time visual feedback to the surgical team, showing the precise positioning and movement of the patient, imaging system itself, and any instruments. A display interface 118 suitable for use is the 13" iPad Air, commercially available from Apple Computer, Inc. Cupertino, CA, USA, however, other commercially available surgical monitor may be used. As noted previously, the display interface may be located remotely from the computer 116 to facilitate more convenient positioning of the display interface 118 for the surgeon during the procedure.

Method of Operation

Figure 2A:
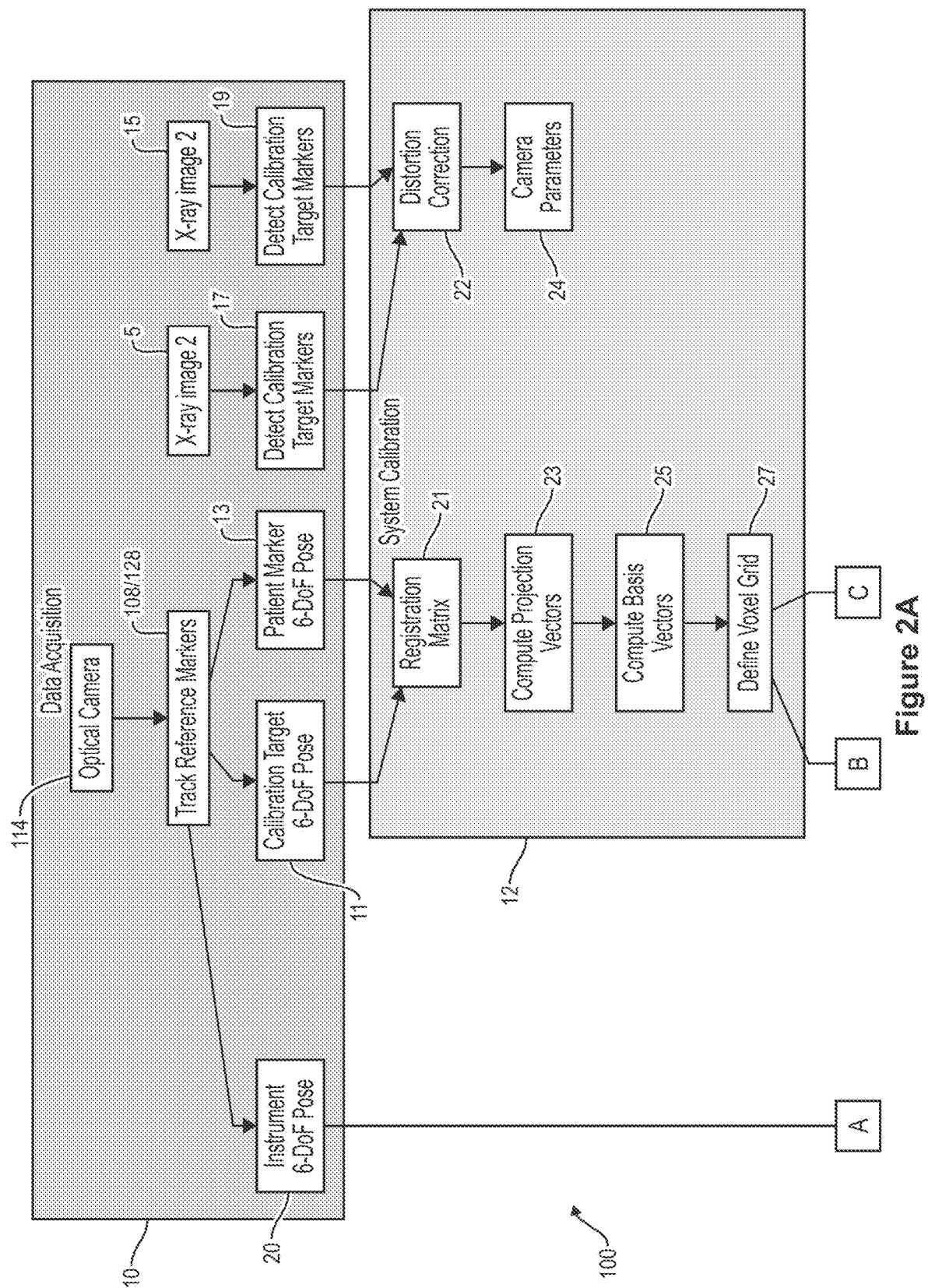
FIGS. 2A-B conceptually illustrate a more detailed process flow of the overall methods performed by the surgical navigation system in accordance with the disclosure.
Figure 2B:
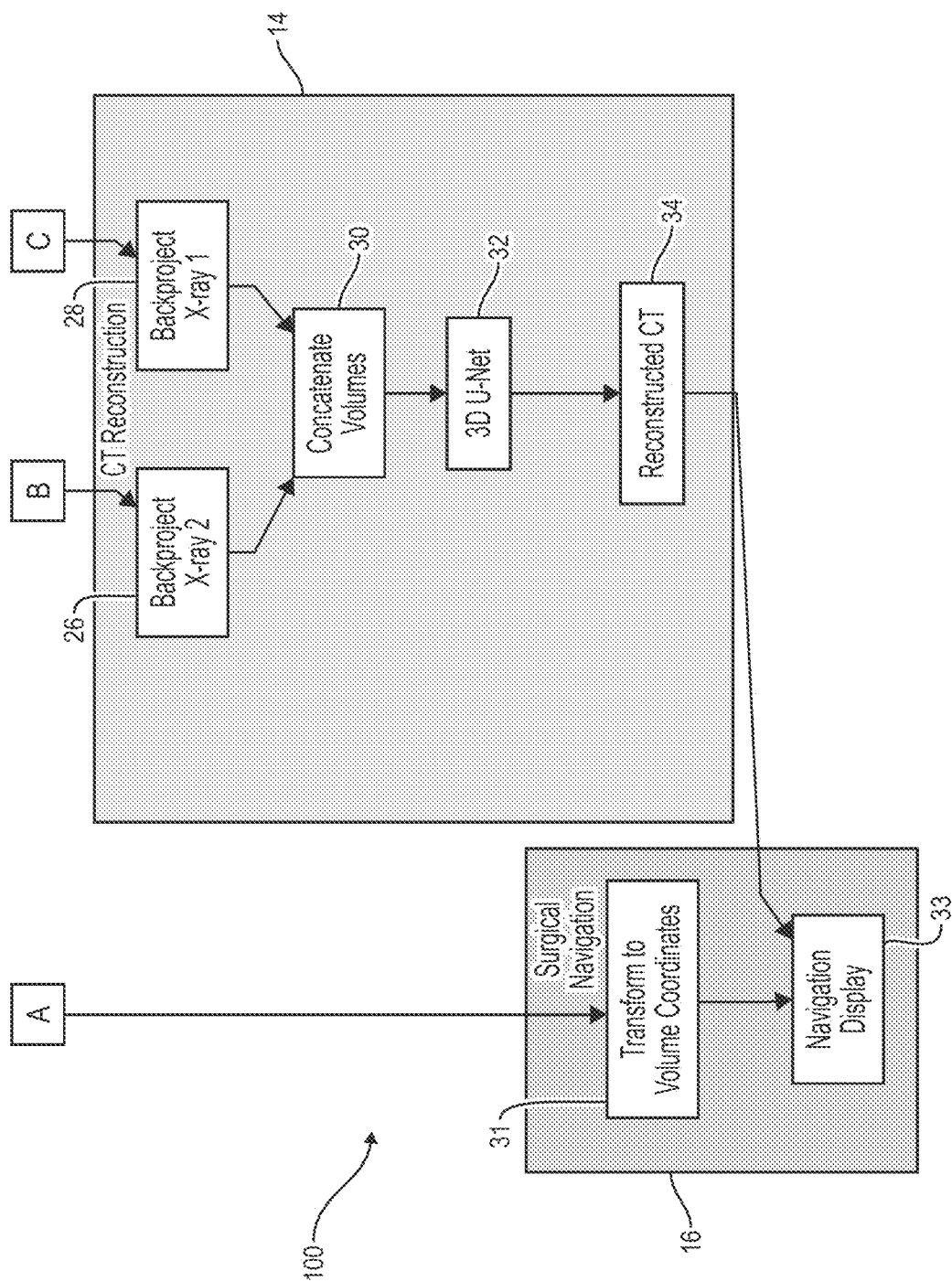

FIGS. 2A-B collectively illustrates a conceptual process flow 100 of the overall methods performed by the surgical navigation system 110 in accordance with the disclosure. Process flow 100 comprises a data acquisition phase 10, a system calibration phase 12, a CT volume reconstruction phase 14, and a surgical navigation phase 16. In initial setup, the camera 114 along with integrated radiation detection device 112 are positioned in the operating room within the surgical field. Reference marker 108 is disposed on or near the patient anatomy. Reference marker 128 is disposed on calibration target 111 which is attached to radiographic image detector 115A.

In the data acquisition phase 10, optical tracking of data for registration purposes is performed. Camera(s) 114 continuously capture images of the surgical field, including reference markers 108 and 128. Detection device 112 monitors levels of radiographic signals in the surgical field. When radiation source 115B is triggered, the radiation detection device 112 identifies radiation emissions as over a predetermined threshold and signals computer 116 to start capturing patient and calibration target pose information from the video streams cameras 114. Simultaneously, radiographic image detector 115A captures image 5, e.g. an X-ray. When the radiation detection device 112 indicates that the radiation emission has ended, computer 116 stops capturing pose information. Object recognition software applications within computer 116 recognize the reference markers 108 and 128 within the captured video data, as illustrated by process blocks 11 and 13, respectively, and records for each of the six degrees of freedom reference markers 108 and 128. At substantially the same time, radiographic image detector 115A generates X-ray image 5 which is provided to computer 116. Software algorithms within computer 116 recognizes calibration markers 40 within the X-ray image 5, as illustrated by process block 17. A similar process occur for X-ray image 15, as illustrated by process block 19.

Figure 14:
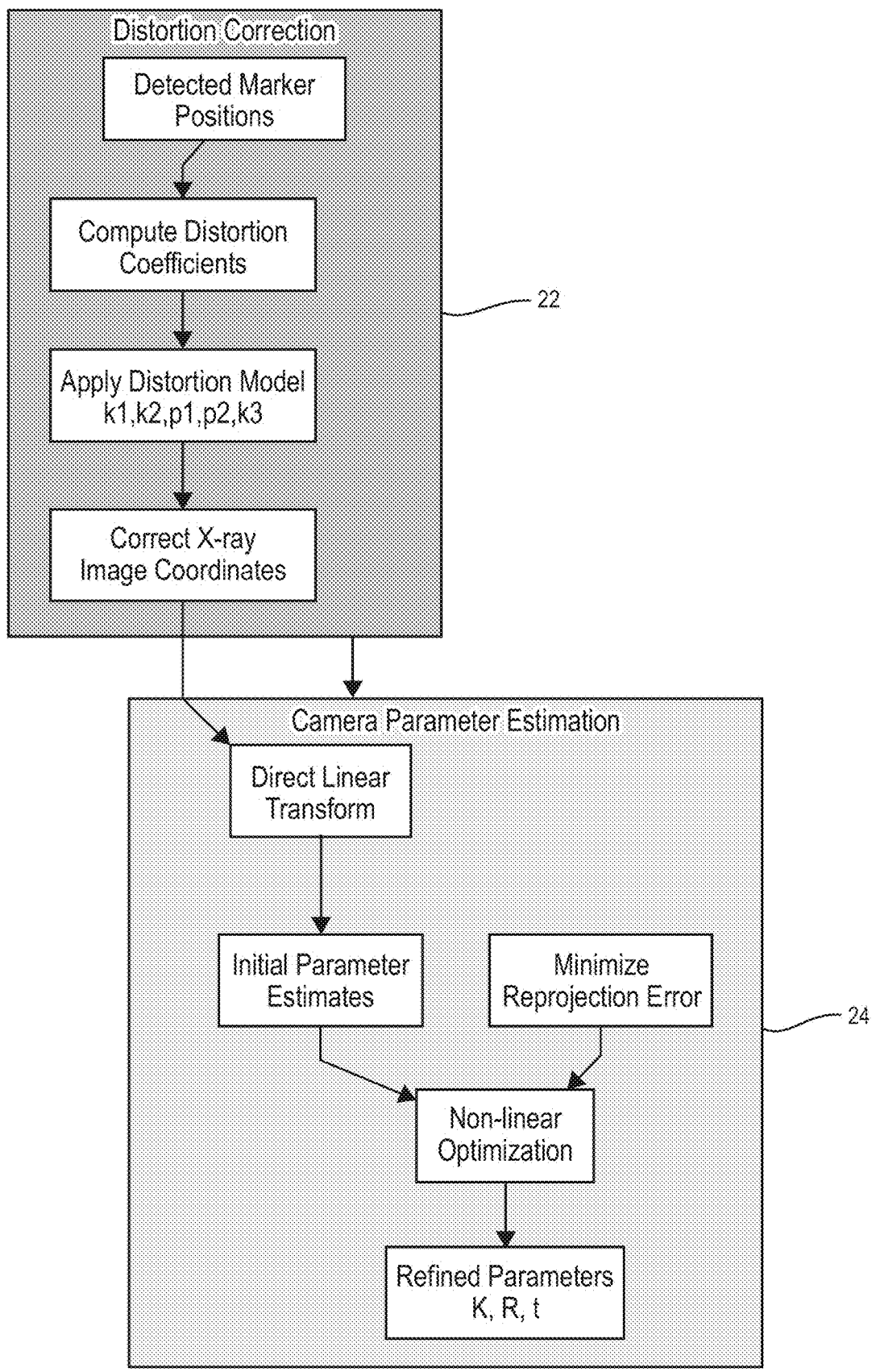
FIG. 14 is a conceptual sub-flow diagram of the distortion correlation and the camera parameter estimation processes of FIG. 2A in accordance with one illustrative embodiment.

Process blocks 21, 22, 23, 24, 25, 27 of FIG. 2A illustrate conceptually the process acts involved in system calibration and grid alignment according to the disclosure. FIG. 14 is a conceptual sub-flow diagram of the distortion correlation and the camera parameter estimation processes of FIG. 2A. As illustrated in FIG. 14, process block 22 illustrates the process for distortion correction including the sub processes of detecting marker positions, computing distortion coefficients, applying the distortion model, and correcting x-ray image coordinates. Further, process block 24 illustrates the process for camera parameter estimation as including the sub processes of direct linear transformation, initial parameter estimates, minimizing reprojection error, non-linear optimization and refining parameters, as illustrated in FIG. 14.

Figure 15:
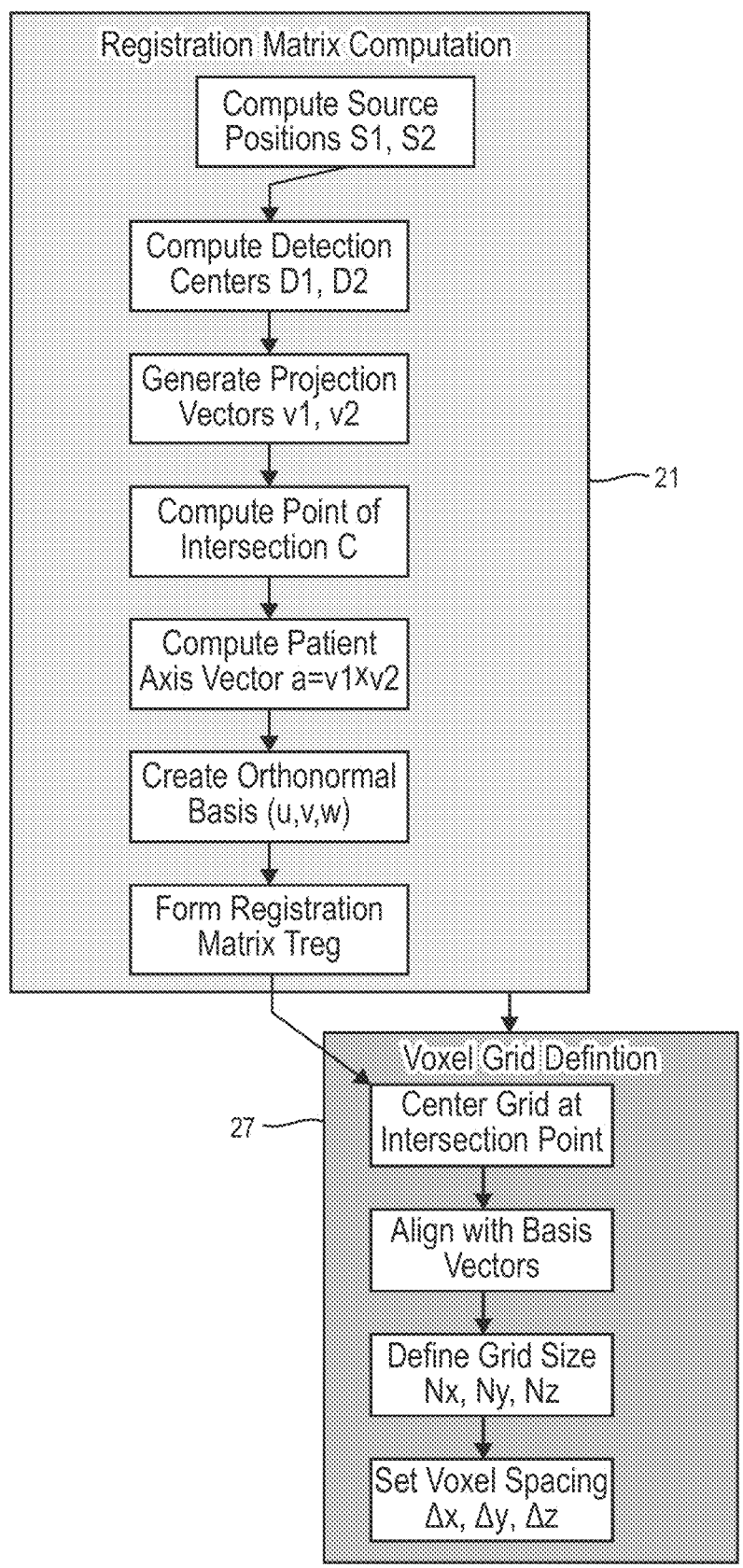
FIG. 15 is conceptual sub-flow diagram of the registration transform calculation and the voxel grid definition processes of FIG. 2A in accordance with one illustrative embodiment.

FIG. 15 is conceptual sub-flow diagram of the registration transform calculation and the voxel grid definition processes of FIG. 2A. The process acts and mathematical basis for the computer executable algorithms represented by process blocks 11,13, 27,19, 22 and 24 are explained in greater detail with reference to process flow 105 of FIG. 3. As illustrated in FIG. 15, process block 21 illustrates the process for registration transform computation as including the sub processes of computing source positions S1 and S2, computing detector centers D1 and D2, generating projection vectors V1 and V2, computing a point of intersection C, a patient access vector as a=V1×V2, creating an orthogonal basis (u,v,w), and forming registration transform $T_{reg}$. Further, process block 27 illustrates the process for camera parameter voxel grid definition as including the sub processes of defining the center of the grid as the intersection point of the vectors, aligning the grid center with the basis vectors, grid size (Nx, Ny, Nz), setting voxel spacings as the individual deltas of (x, y, z), as illustrated in FIG. 15.

The process acts and mathematical basis for the computer executable algorithms represented by process blocks of FIGS. 2A-B are explained in greater detail with reference to process flows of FIGS. 3, 12-16.

Object recognition software, such as Ultralytics YOLO, version 8 or higher, commercially available from www.Ultralytics.com, is used to capture positional information of a surgical instrument 119 relative to the processed pose information of the patient, as illustrated by process block 20. In the surgical navigation phase 16, as described in greater detail herein, the display interface 118 displays the real-time position and movement of surgical instruments relative to the patient, allowing the surgical team to make precise adjustments, without further capturing of patient pose information.

Figure 16:
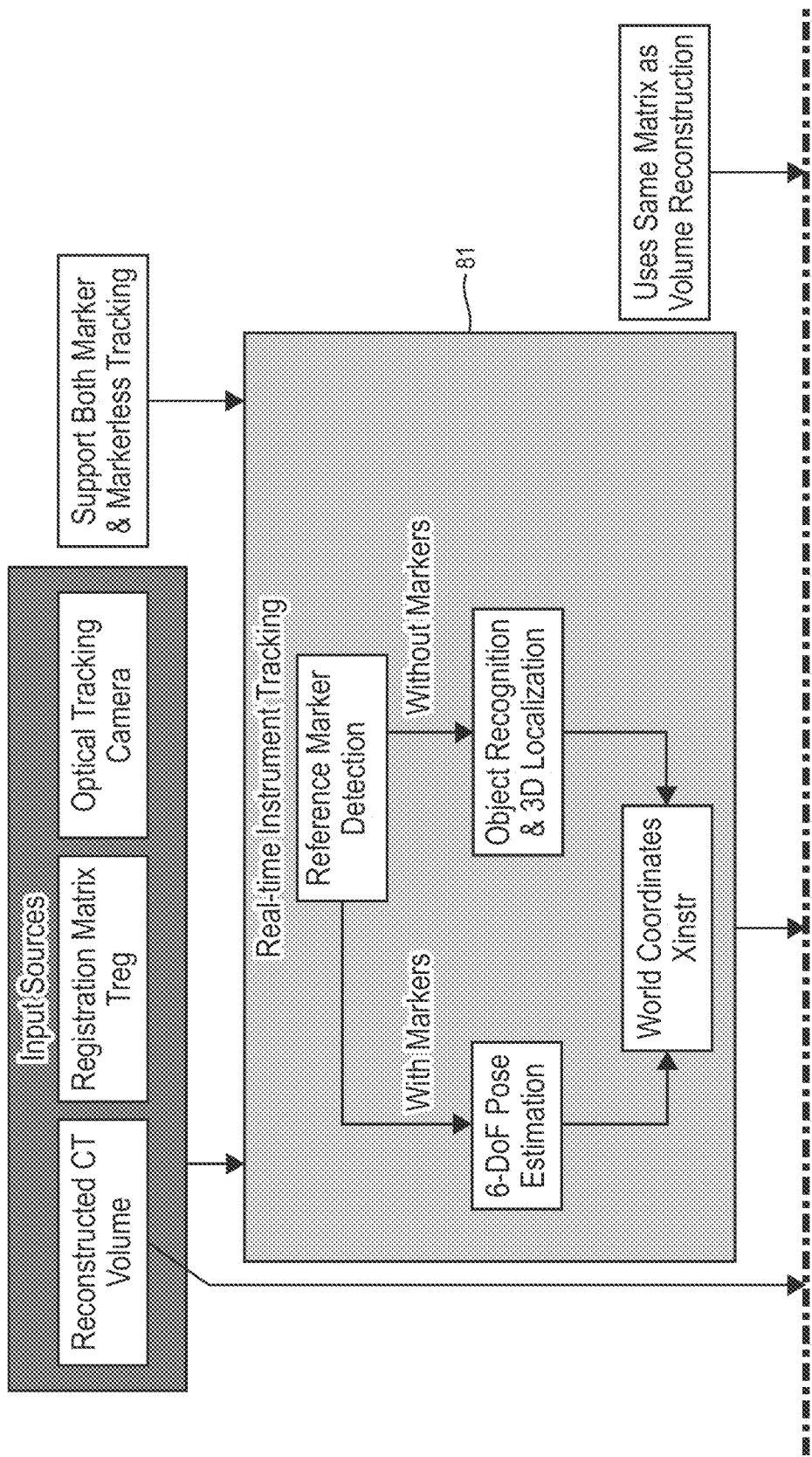
FIG. 16 is conceptual sub-flow diagram of the surgical navigation process processes of FIGS. 2A-B in accordance with one illustrative embodiment.
Figure 16:
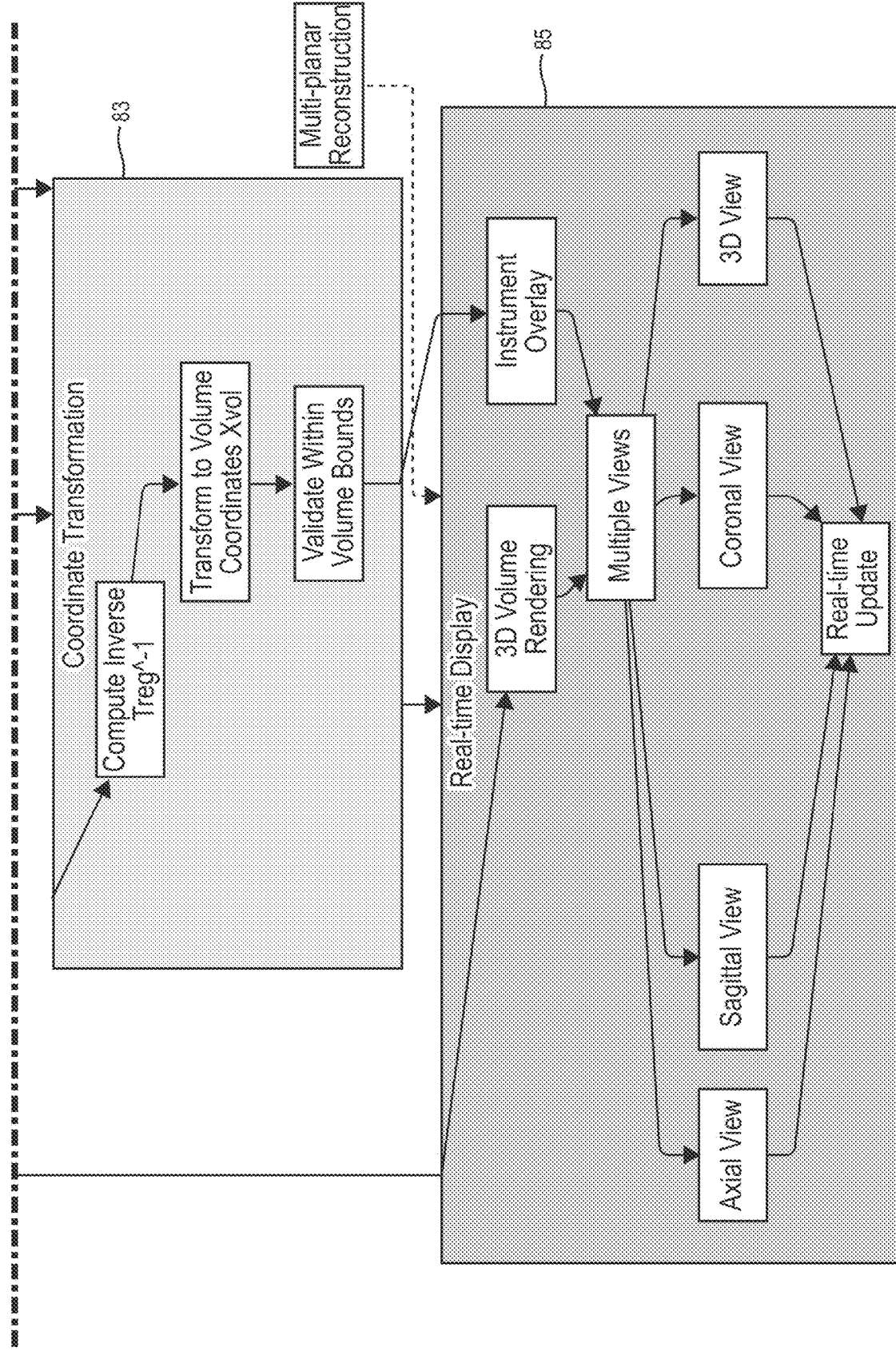

The process acts and mathematical basis for the computer executable algorithms represented by process blocks 11,13, 17,19, 22 and 24 are explained in greater detail with reference to process flow 105 of FIG. 3 which illustrates a process flow for automated reconstruction of a 3D CT volume from 2D X-ray images and display of real-time position and movement of surgical instruments and patient according to the present disclosure. The various acts of process flow 105 may be performed by execution of the computer program instructions 228 stored in the memory 224 and/or storage 227 and controlled by the processor 120 of computer 116, as illustrated in FIG. 16.

Figure 3:
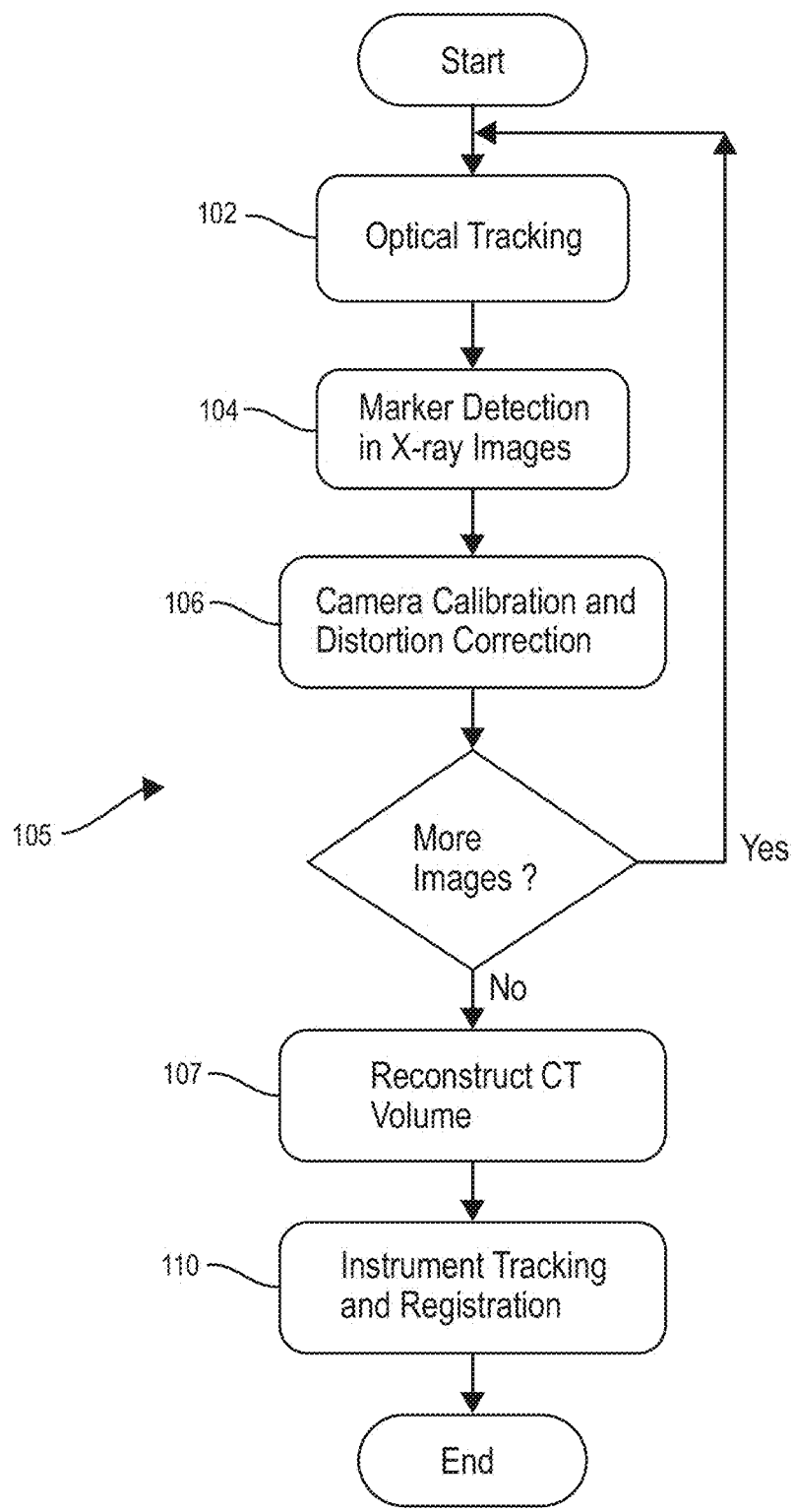
FIG. 3 conceptually illustrates a process flow of the overall methods performed by the surgical navigation system in accordance with the disclosure.
Figure 4:
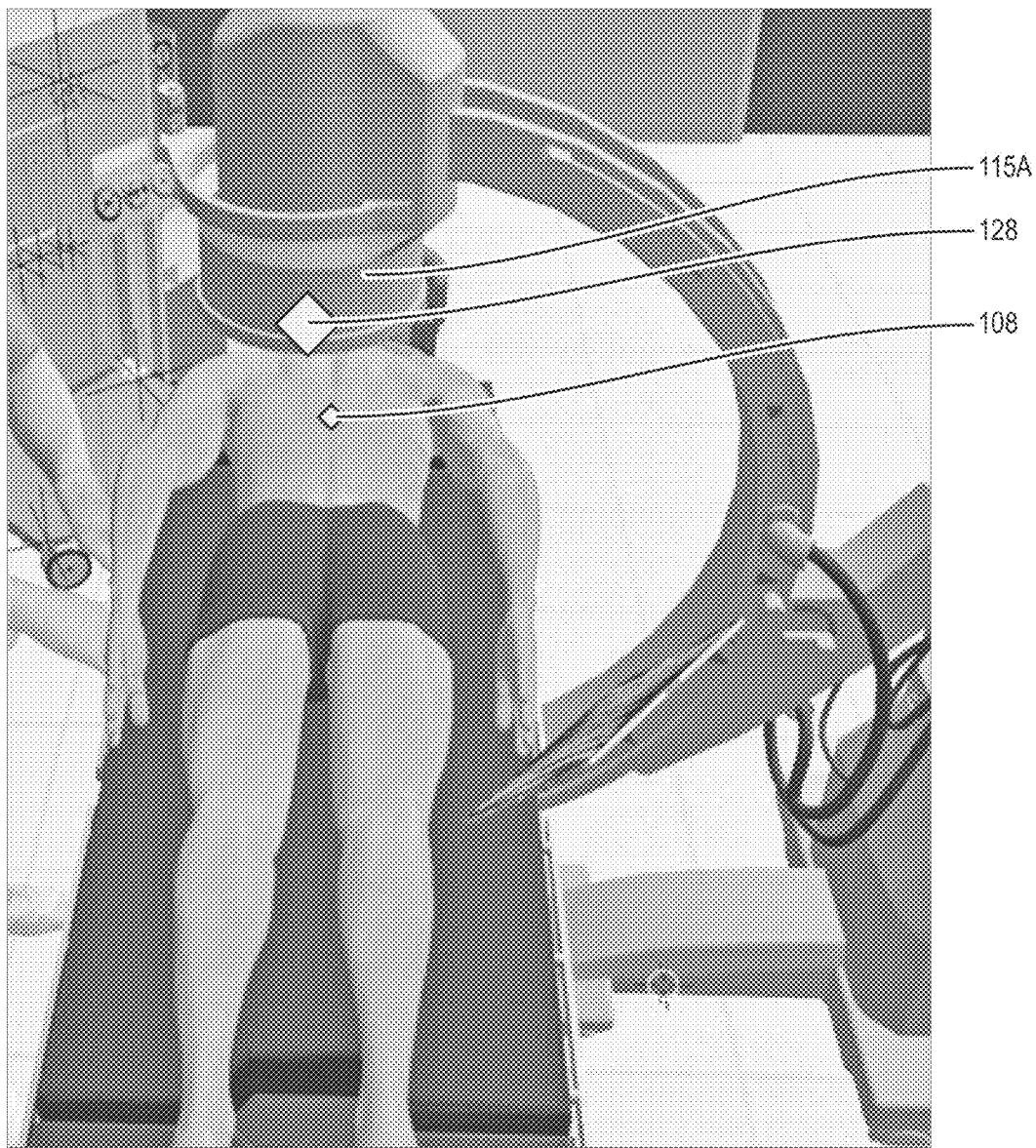
FIG. 4 is a conceptual illustration of the operating environment in which the X-ray C-arm of is posed in an Anterior/Posterior "AP" position in accordance with an illustrative embodiment.
Figure 5:
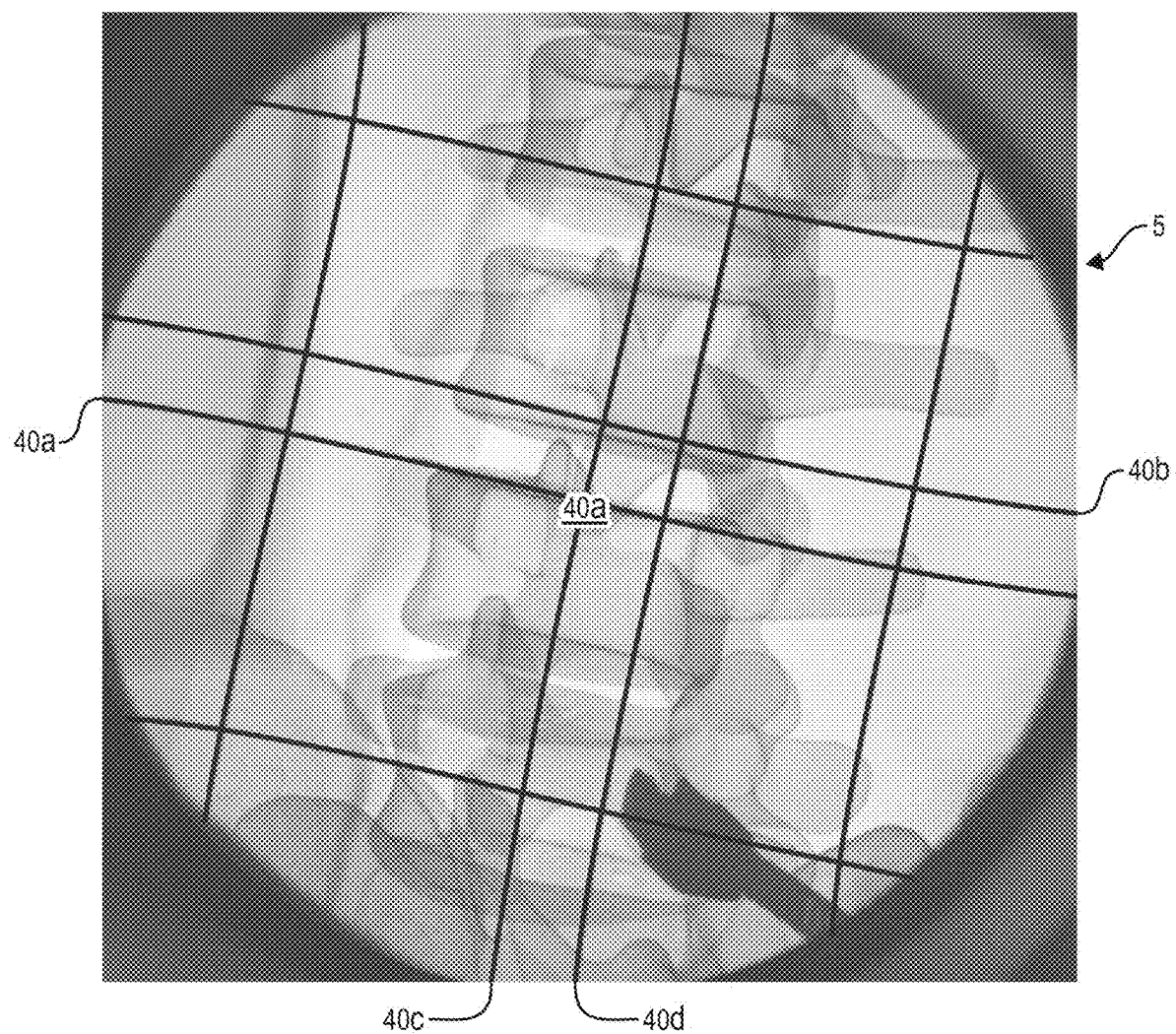
FIG. 5 is a typical "AP" X-ray image generated by a X-ray C-arm in the position of FIG. 4 when used in conjunction with a calibration target having linear markers in accordance with the disclosure.
Figure 6:
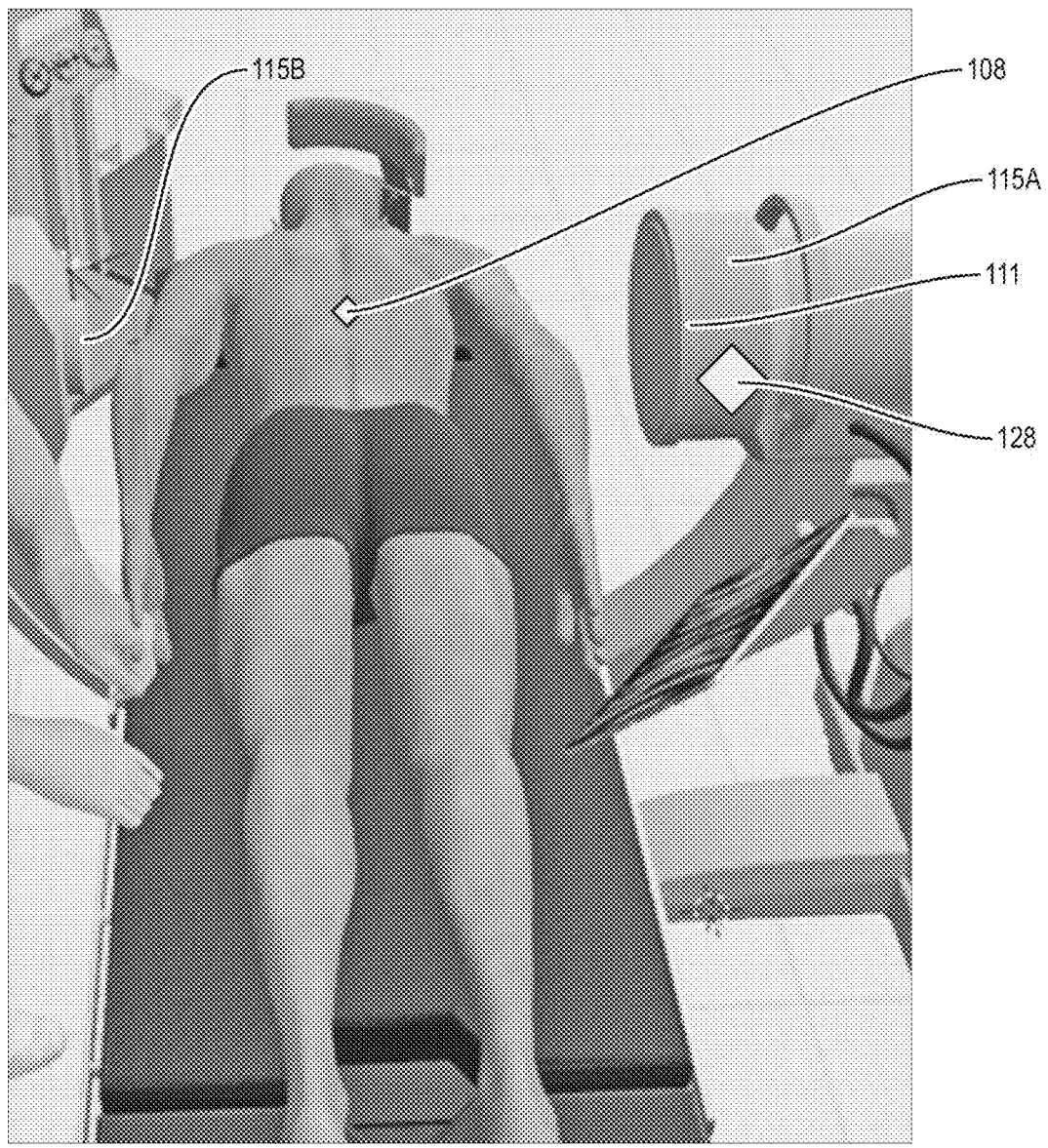
FIG. 6 is a conceptual illustration of the operating environment in which the X-ray C-arm is posed in a "Lateral" position in accordance with an illustrative embodiment.
Figure 7:
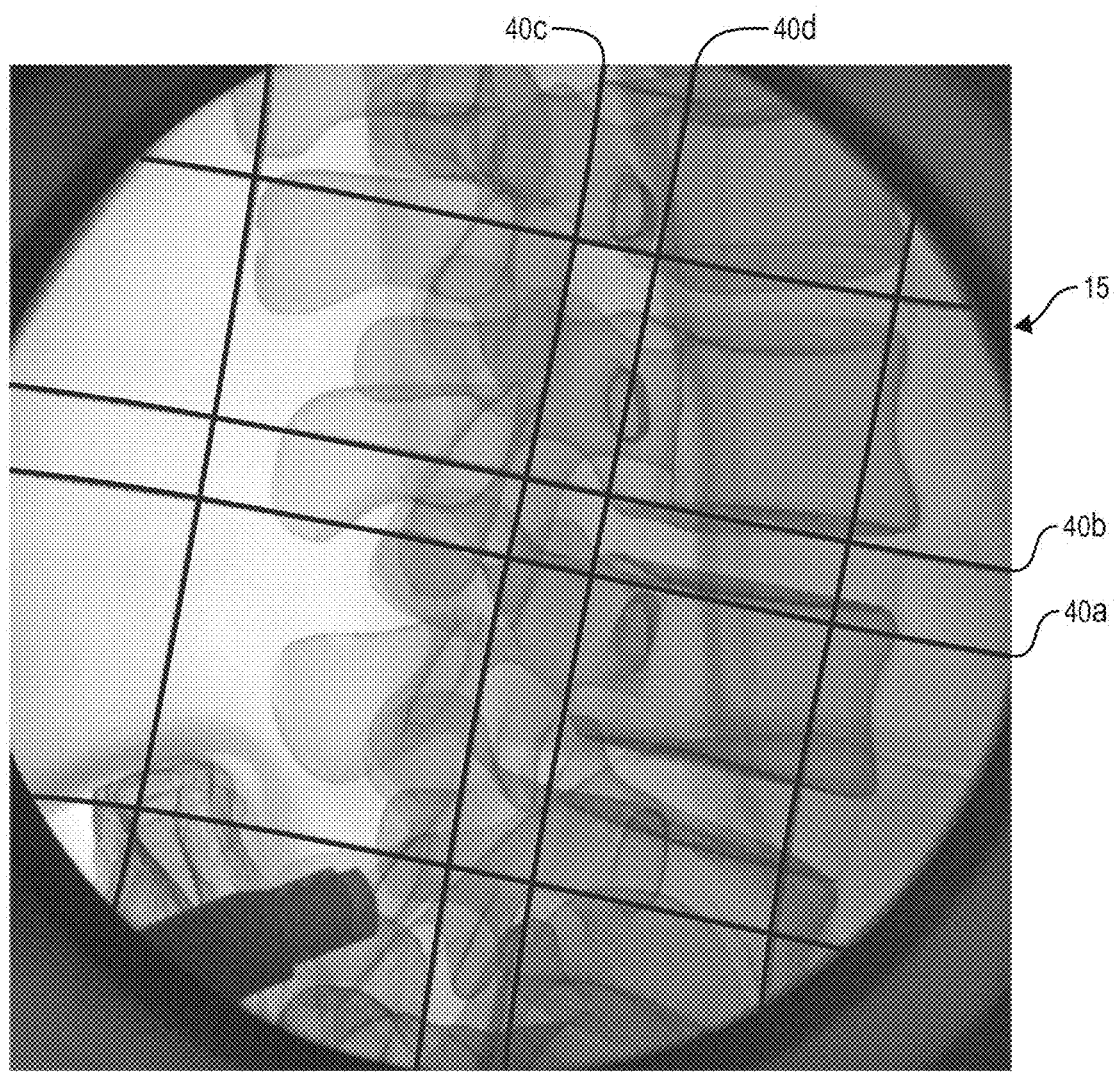
FIG. 7 is a typical "Lateral" X-ray image generated by a X-ray C-arm in the position of FIG. 6 when used in conjunction with a calibration target having linear markers in accordance with the disclosure.

The method of FIG. 3 requires only two 2D X-ray images to perform the reconstruction of the 3D CT volume, but the disclosed method is not limited thereto. The 2D X-ray images 5 and 15 can be obtained using a stand-alone X-ray scanner, a CT scanner, or a C-arm CT scanner. At the time of each 2D X-ray capture, the following process actions occur. At process block 102, optical tracking occurs, where the optical camera 114 detects the reference markers 108 and 128 and records the records the six degrees of freedom (6-DoF) ($R_p$, $t_p$) for the patient reference marker 108 and ($R_c$, $t_c$) for the calibration target marker 128. Optical camera 114 further tracks surgical instruments 119 either through markers attached to the instruments or using object recognition and 3D localization algorithms.

At process block 102, X-ray imaging occurs, with biplanar X-ray image 5 represented by $p_1(u, v)$. The calibration markers 40 within the calibration target 111A are visible in X-ray image 5. A similar process occurs for X-ray image 15 represented by $p_2(u, v)$. Images 5 and 15 captured from different orientations, typically at right angle to each. The calibration markers 40 within the calibration target 111A are also visible in X-ray image 15.

At process block 104, computer executable instructions detect the 2D positions $x_{i,k}^{distorted}$ of the intrinsic calibration markers wires 40 in each X-ray image 5 and 15. The positions of these wire 40 are associated with their known 3D coordinates $X_k$.

At process block 106, computer executable instructions perform camera calibration and distortion correction. Using the correspondences between $X_k$ and $x_{i,k}^{distorted}$, the intrinsic transform K, distortion parameters D, and extrinsic parameters ($R_i$, $t_i$) for each X-ray projection are computed. Non-linear distortions in the X-ray images are determined and corrected using the calibration wire markers 40, as further described in co-pending U.S. patent application Ser. No. 18/974,359, entitled "Wire-Based Calibration Apparatus for X-ray Imaging Systems", filed on an even date herewith.

At process block 110, computer executable instructions perform instrument tracking and registration occurs. The registration transform that transforms instrument coordinates into the volume coordinates is computed and the registration transform is used to track surgical instruments within the reconstructed 3D volume.

A detailed explanation of the mathematical relationships of the various metrics processed as represented by process blocks 102 to 110, as performed by computer instructions executing in computer 116, is provided below. To describe the mathematical relationships, the following notation is defined:

Coordinate Systems:
  world coordinate system is a fixed reference frame in which all other coordinate systems are defined.
  patient coordinate system is attached to the patient, defined by the patient reference marker 108.
  calibration target coordinate system is attached to the calibration target, defined by reference marker 128.
  camera coordinate system is attached to the optical camera(s); with multiple cameras, the output of each optical camera is transformed into a common camera coordinate system.
  detector coordinate system is attached to the radiographic image detector.
  volume coordinate system 70 is defined by the voxel grid 45 centered at the point of intersection 53 and aligned with basis vectors 50 and 51 derived from the image projection vectors 42 and 44.
Points and Projections:
  $X=[X, Y, Z, 1]^T$: homogeneous coordinates of a 3D point in space.
  $x=[u, v, 1]^T$: homogeneous coordinates of a 2D point in the image plane.
Matrices and Vectors:
  K: Intrinsic camera transform of the radiographic imaging system.
  $K_{opt}$: Intrinsic camera transform of the optical camera.
  D: Distortion coefficients for modeling non-linear distortions.
  R, t: Rotation transform and translation vector (extrinsic parameters) relating world and camera coordinates.
  P=K [R|t]: Projection transform mapping 3D points to 2D image points.
Functions:
  $f(X)$: Object function representing the 3D volume to be reconstructed.
  $p_i(u, v)$: X-ray projection image i.

Optical Camera System

The optical camera system of cameras 114 are modeled using a pinhole camera model, which provides a linear relationship between a 3D point and its projection onto the image plane. The projection equation is shown in Equation (1):

$$x \sim K_{opt}[R_{opt}| t_{opt}]X \tag{1}$$

Where:
  $K_{opt}$ is the intrinsic transform of the optical camera, containing parameters such as focal length and principal point.
  $R_{opt}$ and $t_{opt}$ are the rotation transform and translation vector that transform points from the world coordinate system to the camera coordinate system.
  The symbol $\sim$ indicates equality up to a scalar factor, accounting for the homogeneous coordinates.

Understanding the projection geometry of the optical camera is essential for accurately determining the poses of the reference markers and surgical instruments. By establishing this relationship, the disclosed system transforms points between coordinate systems and accurately track the positions and orientations of the patient, calibration target, and instruments.

Reference Markers and Coordinate Transformations

For the patient marker 108, let $X_p$ be the position of a point in the patient coordinate system 62. The optical camera(s) 114 capture the patient reference marker 108, providing its pose ($R_p$, $t_p$) relative to the camera coordinate system. For calibration target marker 128, let $X_c$ represents the position of a point in the calibration target coordinate system. The optical camera(s) 114 provide the pose ($R_c$, $t_c$) of the calibration target's reference marker 128 or reference marker on the sidewall of calibration target. For surgical instruments 119, the positions of surgical instruments $X_{instr}$ can be obtained either with reference arrays for instruments equipped with optical markers detectable by the camera(s) 114, providing poses ($R_{instr}$, $t_{instr}$), or without reference arrays using object recognition and 3D localization algorithms to estimate the instrument poses relative to the patient reference marker 108.

Transformation Between Coordinate Systems

To relate points in the calibration target coordinate systems and instrument coordinate systems to the patient coordinate system, the following transformations shown in Equations (2) and (3) are used:

$$X_p = R_{pc}X_c + t_{pc} \tag{2}$$

-continued $$X_p = R_{pinstr} X_{instr} + t_{pinstr} \quad (3)$$

Where:
$R_{pc} = R_p R_c^T$, $t_{pc} = t_p - R_{pc} t_c$
$R_{pinstr} = R_p R_{instr}^T$, $t_{pinstr} = t_p - R_{pinstr} t_{instr}$ Note that since rotation matrices are orthogonal ($R^{-1} = R^T$), the inverse and transpose are equivalent.

Accurate transformation between coordinate systems facilitates aligning the calibration markers and surgical instruments with the patient's coordinate system. This alignment ensures that the computed poses of the X-ray projections and instruments are consistent with the patient's anatomy, enabling precise navigation.

Detection of Calibration Markers in X-Ray Images

In each X-ray image $p_i(u, v)$, image processing algorithms are employed to detect the 2D positions $x^{distorted\ i,k}$ calibration markers. These positions correspond to known 3D points $X_k$ in the calibration target's coordinate system.

The relationship between the known 3D pointe and their image projections is given by:

$$X_{i,k} \sim K[R_i | t_i] X_k^{world} \quad (4)$$

Where $X_k^{world}$ are the calibration marker coordinates transformed into the world coordinate system:

$$X_k^{world} = R_c X_k + t_c \quad (5)$$

However, when accounting for non-linear distortions, the projection equation becomes:

$$X_{i,k}^{distorted} = \text{Distort}(K[R_i | t_i] X_k^{world}, D) \quad (6)$$

Where:
D represents the distortion coefficients modeling radial and tangential distortions.
Distort(•) is a function that applies the distortion model to the projected points.

By establishing correspondences between the detected 2D positions and known 3D coordinates, and accounting for non-linear distortions, the intrinsic and extrinsic parameters of the radiographic imaging system, as well as the distortion coefficients, can be solved. This calibration enables accurately modeling the radiographic image vectors 50 and 51 and reconstructing the 3D volume 55, especially when image intensifier systems that introduce significant distortions are used with the radiographic image detector 115A.

Camera Calibration and Distortion Correction

The goal of camera calibration is to determine the intrinsic transform K, distortion coefficients D, and the extrinsic parameters ($R_i$, $t_i$) for each X-ray projection i. This process ensures that the system can accurately model the projection geometry, correct for non-linear distortions, and relate image points to points in 3D space.

The disclosed algorithm for calibration includes the following process acts:

Data Collection:
Collect a set of distorted image points $\{x_{i,k}^{distorted}\}$ corresponding to the detected calibration markers 40 in each X-ray image 5 and 15.
Ensure that a sufficient number of markers 40 are detected to provide a well-constrained system, covering the image plane to model distortions effectively.

Correspondence Establishment:
Transform the known 3D coordinates $X_k$ from the calibration target coordinate system to the world coordinate system using the pose ($R_c$, $t_c$):

$$X_k^{world} = R_c X_k + t_c$$

Establish correspondences between each distorted image point $x_{i,k}^{distorted}$ and its transformed 3D point $X_k^{world}$.

Initial Estimation Using Direct Linear Transformation (DLT):
Correct the distorted image points using an initial guess of the distortion coefficients to obtain undistorted points $x_{i,k}$.
Set up the projection equations for each correspondence:

$$X_{i,k} \sim K[R_i | t_i] X_k^{world}$$

Convert the equations into a linear system and solve for the parameters using singular value decomposition (SVD).
Obtain an initial estimate of K, D, $R_i$, and $t_i$.

Nonlinear Optimization (Refinement):
Define the reprojection error as:

$$E = \sum_{i,k} \left\| X_{i,k}^{distorted} - \text{Distort}\left(\pi(K, R_i, t_i, X_k^{world}), D\right) \right\|^2$$

Where $\pi$ is the projection function mapping 3D points to 2D image points using the current estimates.
Use nonlinear optimization techniques, e.g., Levenberg-Marquardt algorithm) to minimize the reprojection error E.
Update the estimates of K, D, $R_i$, and $t_i$ iteratively until convergence.

Validation:
Assess the accuracy of the calibration by projecting the 3D points using the calibrated parameters and comparing them to the detected distorted image points.
Compute statistical measures such as the mean reprojection error to quantify the calibration quality.

Intrinsic Parameters and Distortion Coefficients
Intrinsic Transform K:

$$K = \begin{bmatrix} f_x & 0 & c_x \\ 0 & f_y & c_y \\ 0 & 0 & 1 \end{bmatrix} \quad (7)$$

Where:
 $f_x$, $f_y$ are the focal lengths in pixels along the x and y axes.
 $c_x$, $c_y$ are the coordinates of the principal point.
Distortion Coefficients D:

$$D = [k_1, k_2, p_1, p_2, k_3] \qquad (8)$$

Where:
 $k_1$, $k_2$, $k_3$ are radial distortion coefficients.
 $p_1$, $p_2$ are tangential distortion coefficients.
Precise calibration, including distortion correction, ensures that the geometric relationships between the 3D scene and the 2D images are accurately captured. Correcting non-linear distortions is essential when using X-ray image intensifier systems, as these distortions can significantly affect the accuracy of the back-projection and reconstruction processes.

Reconstruction of 3D CT Volumes from X-Ray Projections

FIGS. 10-13 illustrate a process for automated reconstruction of a 3D CT volume from 2D X-ray images and display of real-time position and movement of surgical instruments and patient according to the present disclosure. The various acts of process flow 130 may be performed by execution of the computer program instructions 228 stored in the memory 224 and/or storage 227 and controlled by the processor 120 of computer 116, as illustrated in FIG. 14.

Figure 10:
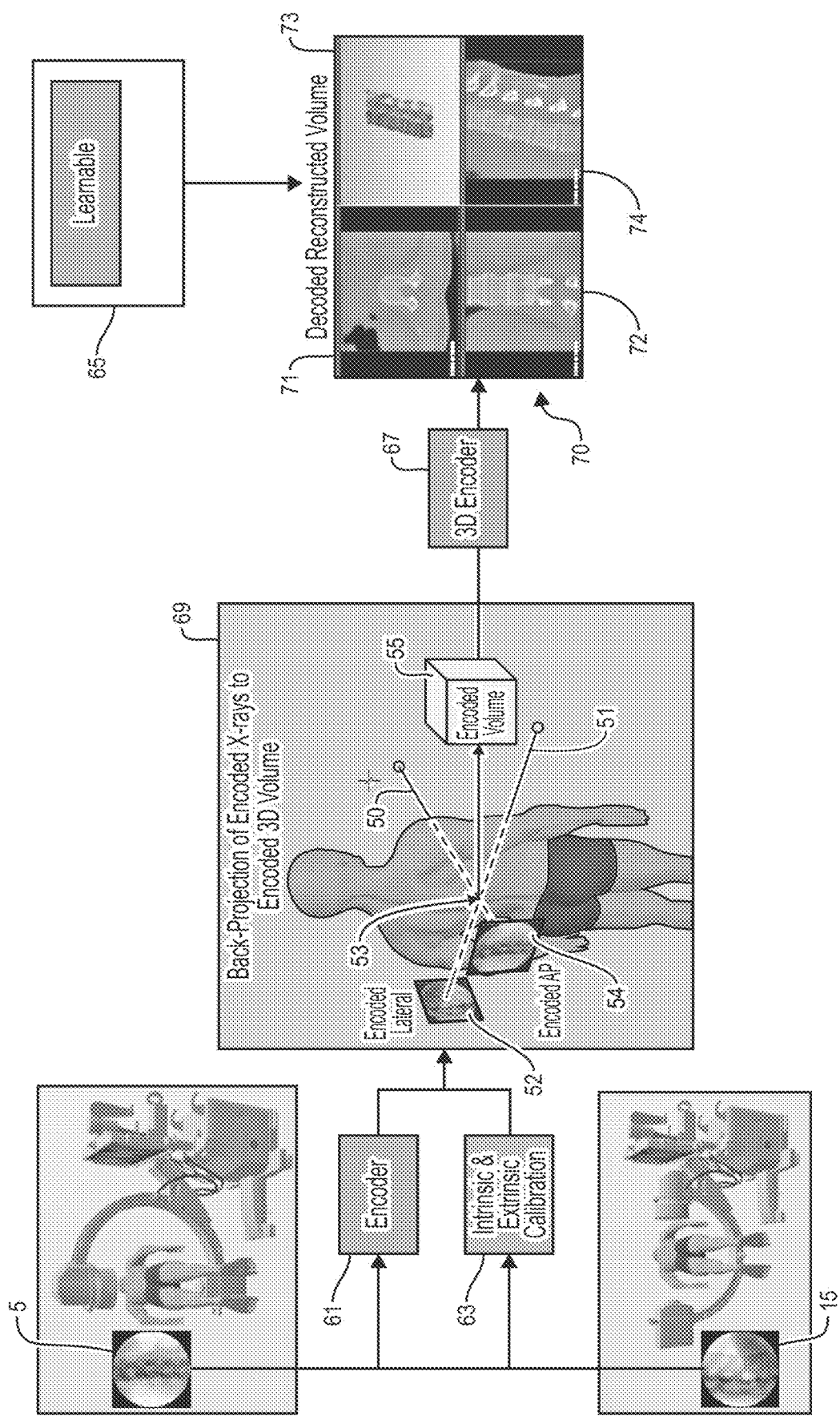
FIG. 10 is a conceptual flow diagram of the processes performed for reconstruction of 3D volumes from biplanar X-ray projections in accordance with an illustrative embodiment.
Figure 11A:
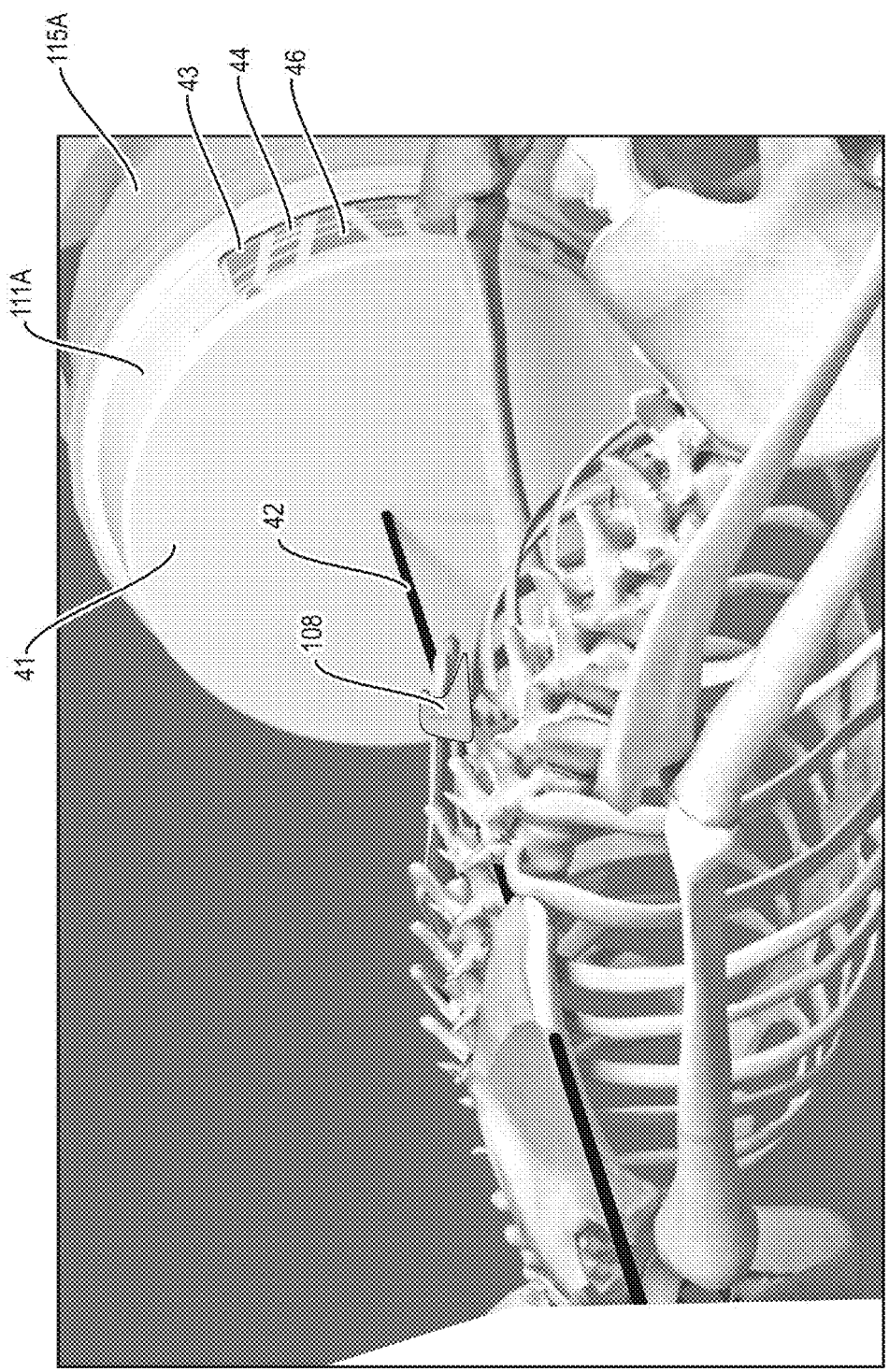
FIG. 11A-C illustrates conceptually the relationship between computed central rays of by biplanar images and the voxel grid in accordance with the disclosure.
Figure 11B:
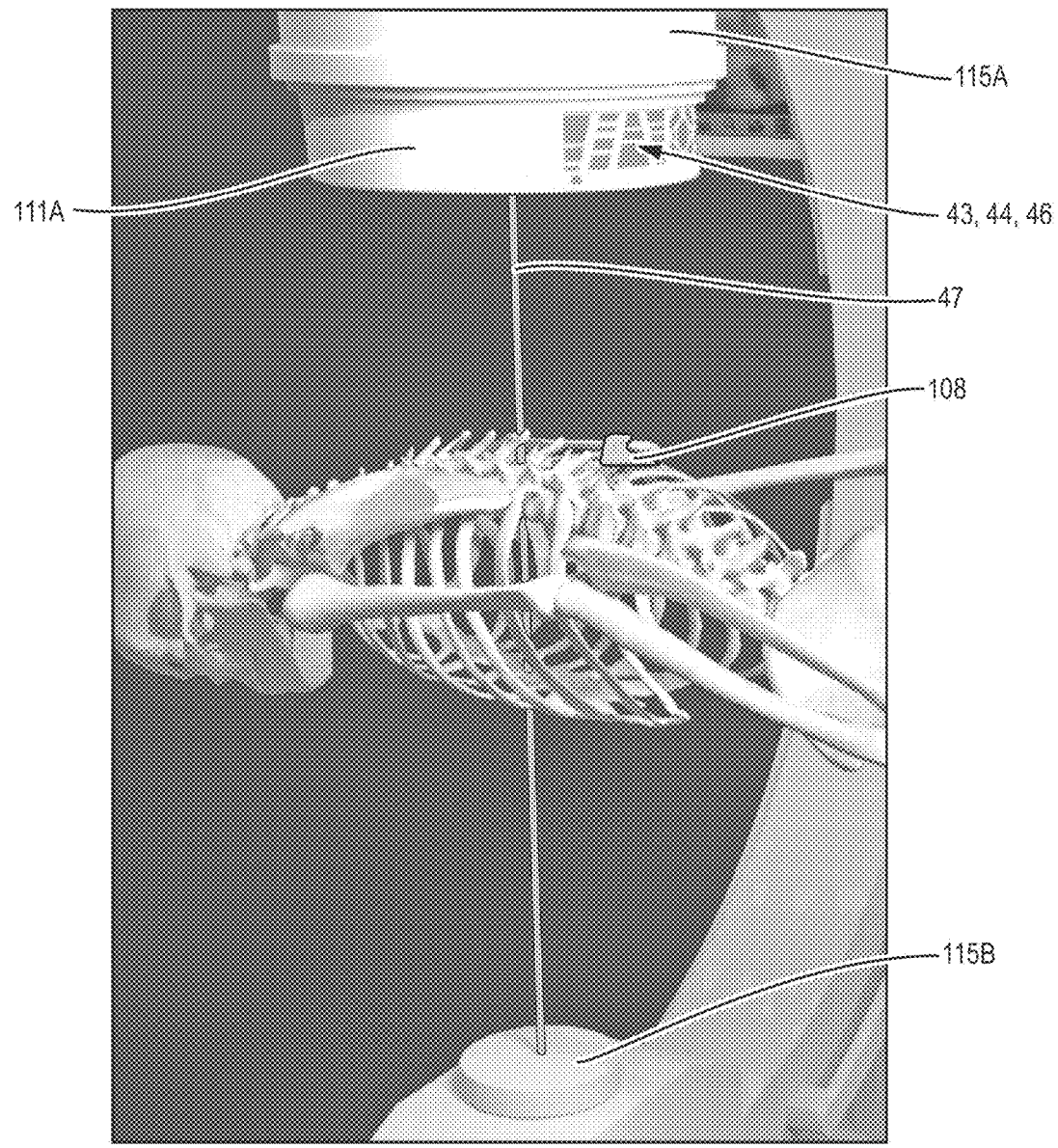
Figure 11C:
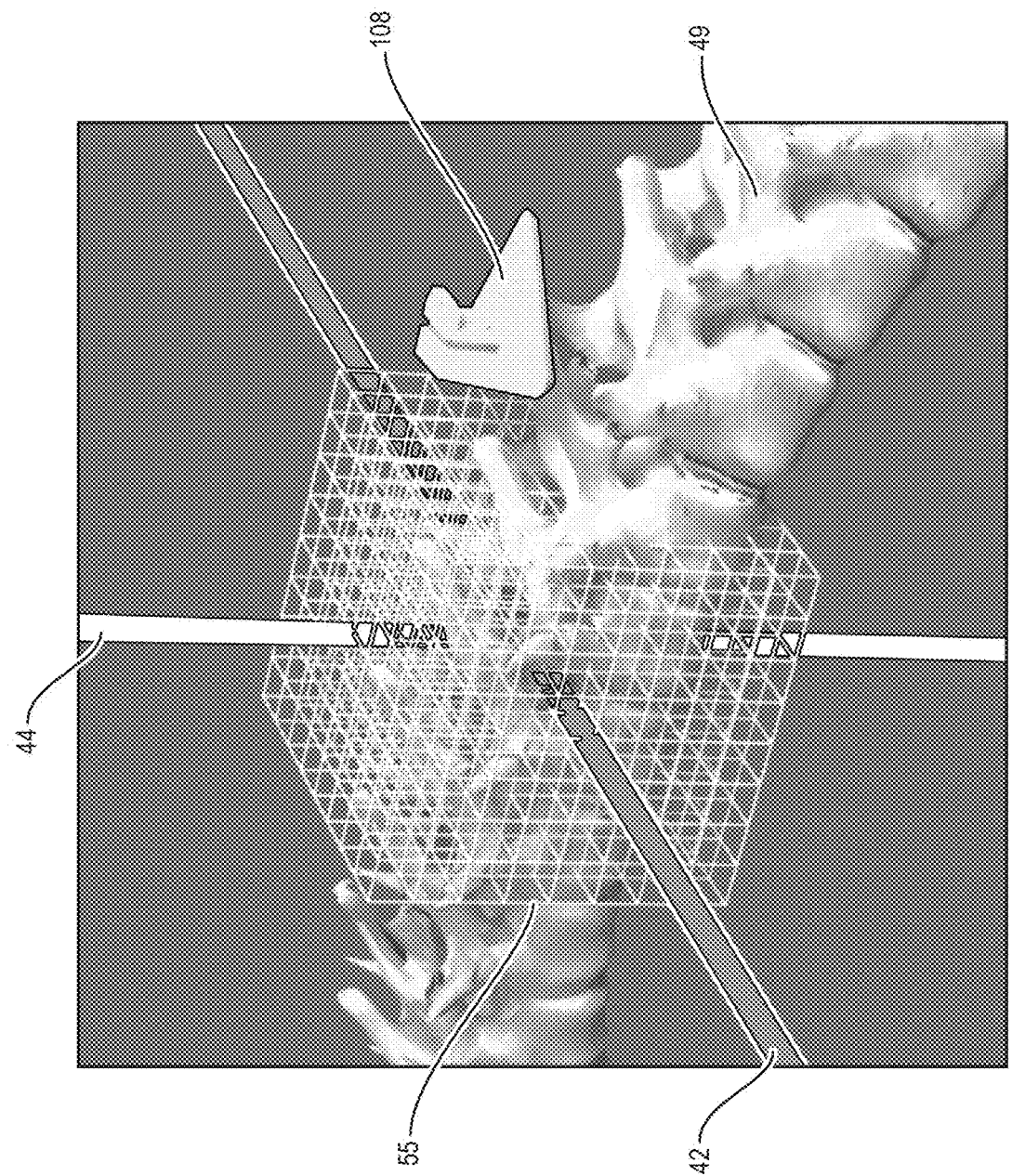

Once the X-ray images are captured, computer executable instructions perform reconstruction of a 3D CT volume 70. The calibrated poses ($R_i$, $t_i$) and intrinsic transform K are used to model X-ray projections using a generalized Radon transform, as further described in co-pending U.S. patent application Ser. No. 18/974,545, entitled "System and Method for Reconstruction of 3D Volumes from Biplanar X-ray Images", filed on an even date herewith. As illustrated in FIG. 10, a pair of radiographic images 5 and 15 are encoded as illustrated by encoder process block 61 and calibrated for intrinsic and extrinsic distortions, as illustrated by calibration process block 63. From the resulting pair of encoded radiographic images of 52 and 54, image projections are used to form basis vector 50 and 51, and their intersection at a central point 53 used for generating the registration transform, as illustrated by process block 69. The encoded radiographic images of 52 and 54 are back projected into a encoded volume 55 which is then decoded, as illustrated by process block 67, into a three-dimensional volume 70 capable of multiplanar views, including axial, sagittal, coronal, and 3D views of the three-dimensional volume. Back-projection and deep learning techniques may be used to reconstruct the 3D volume of CT quality images from the biplanar X-ray images 5 and 15. The three-dimensional volume 70 may be generated with the assistance of deep learning module 65, as illustrated. FIGS. 11A-C illustrate conceptually the relationship between computed central rays 42 and 47 of the radiation imaging system, the reference marker 108, the reference marking on the calibration target 111A, and the voxel grid 45 relative to a portion of patient anatomy 49.

Figure 12:
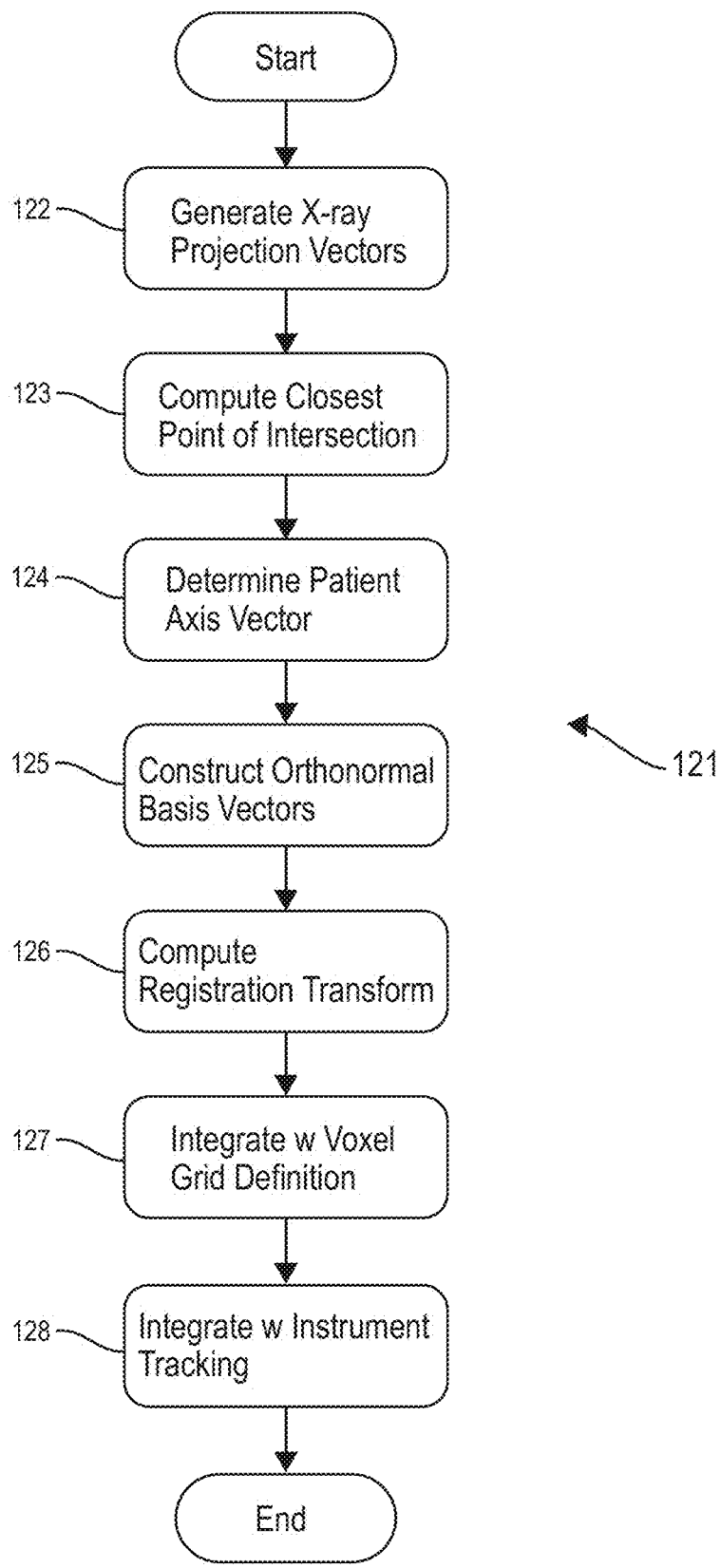
FIG. 12 is a flow diagram of the processes performed for generating a registration transform in accordance with an illustrative embodiment.
Figure 13:
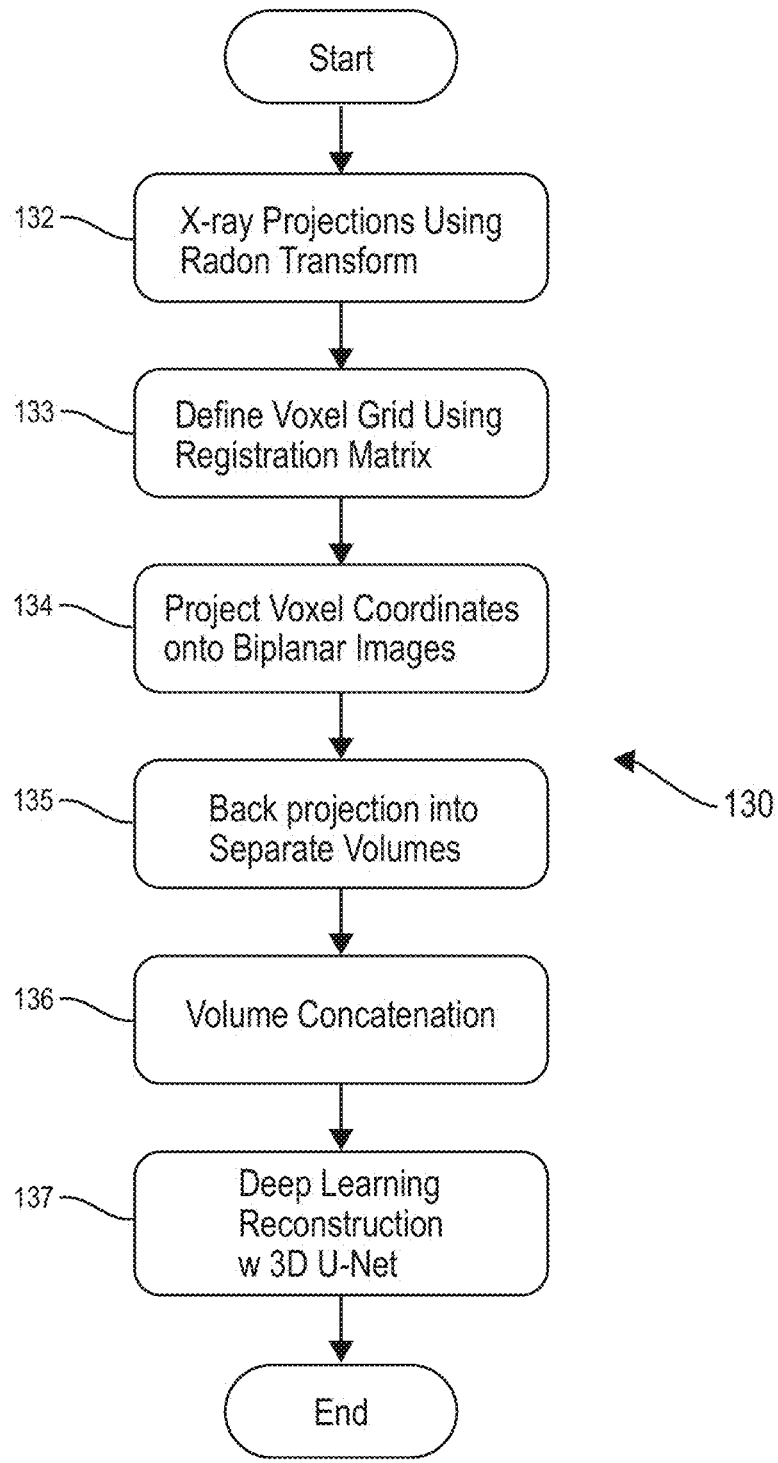
FIG. 13 illustrates conceptually the process for generation of volume of a subject's anatomical elements in accordance with one illustrative embodiment.

The algorithmic acts of reconstruction the 3D volume, as represented by process block 107 of FIG. 3, are described below in greater detail with reference to flowchart 121 of FIG. 12. With the calibrated poses ($R_i$, $t_i$), intrinsic transform K, and distortion coefficients D, the system can reconstruct the 3D CT volume $f_{out}(X_{vox})$ from the two X-ray projections $p_1(u, v)$ and $p_2(u, v)$. The reconstruction process of the 3D CT volume is as follows. At process block 132 computer executable instructions perform modeling of the X-ray projections using the generalized Radon Transform to represent the projections based on the object's attenuation properties. The X-ray projections are modeled by integrating the object function $f(X)$ along rays defined by the imaging geometry. For each projection i:

$$p_i(u, v) = \int_{l_{min}}^{l_{max}} f(S_i + l\, d_i(u, v))\, dl \qquad (9)$$

Where:
 $S_i$ is the position of the X-ray source for projection i.
 $d_i(u, v)$ is the unit direction vector from the X-ray source to the detector pixel at (u, v).
 $l_{min}$ and $l_{max}$ define the limits of integration along the ray, typically encompassing the region of interest.

The generalized Radon transform accounts for the arbitrary poses and geometries of the imaging system, which is essential when dealing with a mobile C-arm that can assume various orientations. Modeling such projections accurately facilitates greater fidelity of the reconstruction.

At process block 133 computer executable instructions perform definition of a 3D grid of voxel coordinates using the registration transform, centered at the point of intersection and aligned with the basis vectors. An essential step in the reconstruction process is the definition of a 3D grid of voxel coordinates that represents the volume to be reconstructed. The voxel grid is defined using the registration transform $T_{reg}$, ensuring consistency between the navigation and reconstruction components.

To define the Voxel Grid let $N_x$, $N_y$, $N_z$ be the number of voxels along each axis, and $\Delta x$, $\Delta y$, $\Delta z$ be the voxel sizes. The coordinates of each voxel $X_{vox}$ are computed as:

$$X_{vox}(i, j, k) = T_{reg} \begin{bmatrix} \left(i - \frac{N_x}{2}\right)\Delta x \\ \left(j - \frac{N_y}{2}\right)\Delta y \\ \left(k - \frac{N_z}{2}\right)\Delta z \\ 1 \end{bmatrix} \qquad (10)$$

Where i=0, 1, ..., $N_x$−1, and similarly for j and k.

This formulation ensures that the voxel grid is centered at the point C and aligned along the basis vectors (u, v, w) defined by the registration transform. An additional motivation for defining the voxel grid 45 using the registration transform 69 is to ensure consistency between the coordinate systems used for instrument tracking and volume reconstruction. This alignment guarantees that when projected onto the two X-ray images, the voxel grid points will generally fall within the field of view of the X-ray images 5 and 15.

At process block 134 computer executable instructions project each voxel coordinate onto the biplanar images using the calibration matrices, accounting for any corrected distortions. To back-project using these grid points, each voxel coordinate $X_{vox}$ is projected onto each of the biplanar images using their independent intrinsic and extrinsic calibration matrices, accounting for distortion correction:

$$X_i^{distorted} = \text{Distort}\left(K\left(R_i X_{vox}^{world} + t_i\right), D\right) \tag{11}$$

Where:

$X_{vox}^{world}$ is the voxel coordinate in the world coordinate system, obtained by applying $T_{reg}$ to the grid indices. The projection $x_i^{distorted}$ is then normalized to obtain pixel coordinates.

At process block 135 computer executable instructions perform back-projecting each projection into a separate 3D volume, taking into account the imaging geometry. The back-projection for each projection i is performed by accumulating the contributions from the X-ray image $p_i(u, v)$ to each voxel based on the projection of the voxel onto the image:

$$f_{BP_i}(X_{vox}) = p_i(u_i, v_i) w_i(X_{vox}) \tag{12}$$

Where:

($u_i$, $v_i$) are the pixel coordinates corresponding to the distorted projection $x_j^{distorted}$.

$w_i(X_{vox})$ is a weighting function accounting for factors such as the distance from the source to the voxel and the angle of incidence.

At process block 136 computer executable instructions perform volume concatenation. That is, combining the back-projected volumes to form a multichannel input. The two back-projected volumes are concatenated along a new dimension (channel axis) to form a multichannel volume $f_{concat}(X_{vox}, c)$:

$$f_{concat}(X_{vox}, c) = \begin{cases} f_{BP_1}(X_{vox}), & c = 1 \\ f_{BP_2}(X_{vox}), & c = 2 \end{cases} \tag{13}$$

At process block 137 computer executable instructions perform cause trained 3D U-Net model 66 to map the concatenated volume 67 to the final 3D volume 70. The disclosed method employs a 3D U-Net U to map the concatenated volume to the reconstructed CT volume:

$$f_{out}(X_{vox}) = U(f_{concat}(X_{vox}, c)) \tag{14}$$

In embodiments, the U-Net architecture is suitable due to its Encoder-Decoder structure comprising a contracting path (encoder) that captures context and an expansive path (decoder) that enables precise localization. The U-Net architecture utilizes skip connections wherein feature maps from the encoder are combined with corresponding decoder layers, preserving spatial information. Further, the U-Net architecture utilizes 3D convolutions wherein the network operates on volumetric data, using 3D convolutional layers to capture spatial relationships in all three dimensions.

Recent advances in deep learning have opened new avenues for solving inverse problems in imaging. Neural networks, particularly convolutional neural networks (CNNs), can learn complex mappings from input data to desired outputs by leveraging patterns learned from large datasets. By integrating optical tracking with advanced computational methods, the disclosed system overcomes traditional limitations and provide practical solutions for intraoperative imaging and instrument tracking. The U-Net architecture is well-suited for medical image reconstruction due to its ability to learn complex mappings from input data to output volumes while preserving spatial resolution. It has been successful in various biomedical imaging tasks, demonstrating robustness and effectiveness.

Integration of Voxel Grid Definition into the Reconstruction Process

By defining the voxel grid using the registration transform $T_{reg}$, the system 110 ensures that the reconstructed volume 70 is in the patient coordinate system 60 and consistent with the instrument tracking frame work. This alignment is needed for accurate navigation and ensures that the voxel grid and registration transform share the same center and basis vectors.

An additional motivation for defining the grid using $T_{reg}$ is to ensure that when projected onto the two X-ray images, the grid points will generally fall within the field of view of the X-ray images. The size of the 3D grid in each dimension is chosen accordingly to guarantee that the projected grid points are within the images.

The projection of voxel coordinates onto the biplanar images establishes a direct connection between the spatial domain of the volume and the image domain of the X-ray projections. This step integrates the generalized Radon transform into the reconstruction process, enabling the deep learning model to effectively learn the mapping from limited-angle projections to the full 3D volume.

Instrument Tracking and Registration

To enable real-time tracking of surgical instruments within the reconstructed volume, the disclosed system 110 computes a registration transform that transforms instrument coordinates (in the patient coordinate system) into the volume coordinates of the generated 3D volume 70. Such registration transform encompasses both positional and rotational information and used to define the center and orientation of the voxel grid 45 for back projection and reconstruction, ensuring consistency between navigation and imaging.

The disclosed system and method facilitates automatic registration of the surgical instruments 119, especially in minimally invasive procedures where the patient's anatomy does not need to be exposed for registration. The disclosed automatic process enhances surgical efficiency and reduces patient trauma.

The algorithmic acts of process block 110 of FIG. 2, are described below in greater detail with reference to flowchart 121 of FIG. 12 and also FIG. 16. At process block 122 execution of computer instructions causes generation of X-ray projection vectors. Specifically, for each X-ray projection i, define a vector $v_i$ from the X-ray source 15A position to the central point of the X-ray detector 15B. The position of the X-ray source $S_i$ in the patient coordinate system is given by:

$$S_i = R_{pc}(-R_i^T t_i) + t_{pc} \tag{15}$$

The central point of the X-ray detector $D_i$ in the patient coordinate system is computed using:

$$D_i = R_{pc}(-R_i^T t_i + R_i^T K^{-1} x_0) + t_{pc} \quad (16)$$

Where:
$x_0 = [c_x, c_y, 1]^T$ is the principal point (center) of the detector in homogeneous coordinates.
The projection vector from the source to the detector center is:

$$v_i = D_i - S_i \quad (17)$$

At process block 123 execution of computer instructions causes computation of the closest point of intersection of the projection vectors. The two vectors $v_1$ and $v_2$ generally do not intersect due to slight misalignments and noise, a point C that minimizes the distance between the two lines defined by $(S_1, v_1)$ and $(S_2, v_2)$ is computed.
Using scalars s and t that minimize:

$$\|(S_1 + sv_1) - (S_2 + tv_2)\|^2 \quad (18)$$

Solving this system yields s and t, and the point of closest approach C is taken as the midpoint between $S_1+sv_1$ and $S_2+tv_2$:

$$C = \frac{(S_1 + sv_1) + (S_2 + tv_2)}{2} \quad (19)$$

At process block 124 execution of computer instructions causes determination of the patient axis vector. The patient axis vector a is determined by the cross product of the two projection vectors as in Equation (20):

$$a = v_1 \times v_2 \quad (20)$$

This vector is orthogonal to the plane formed by $v_1$ and $v_2$.
At process block 125 computer executable instructions perform construction of orthonormal basis vectors. A set of orthonormal basis vectors (u, v, w) that define the rotation from the patient reference frame to the volume coordinate system are constructed, as set forth in Equations (21), (22) and (23) below.
First Basis Vector Normalize u:

$$u = \frac{v_1}{\|v_1\|} \quad (21)$$

Second Basis Vector Normalize w:

$$w = \frac{a}{\|a\|} \quad (23)$$

Third Basis Vector Compute:

$$v = w \times u \quad (23)$$

At process block 126 computer executable instructions perform computation of the registration transform. The registration transform $T_{reg}$ is a 4×4 homogeneous transformation transform defined as in Equation (24):

$$T_{reg} = \begin{bmatrix} u & v & w & C \\ 0 & 0 & 0 & 1 \end{bmatrix} \quad (24)$$

This transform transforms points from the volume coordinate system to the patient coordinate system. Its inverse $T_{reg}^{-1}$ is used to transform points from the patient coordinate system to the volume coordinate system.
At process block 127 computer executable instructions perform integration with voxel grid definition. The voxel grid $X_{vox}$ used in the reconstruction is defined using $T_{reg}$, ensuring that the grid's center and orientation match those used for instrument tracking.

$$X_{vox}^{world} = T_{reg} \begin{bmatrix} \left(i - \frac{N_x}{2}\right)\Delta x \\ \left(j - \frac{N_y}{2}\right)\Delta y \\ \left(k - \frac{N_z}{2}\right)\Delta z \\ 1 \end{bmatrix} \quad (25)$$

At process block 128 computer executable instructions perform integration with instrument tracking. Acquiring the pose of an instrument can be done in multiple ways. If instruments have reference arrays, positions $X_{instr}$ from optical tracking is obtained. If instruments are tracked without reference arrays, object recognition and 3D localization algorithms are used to estimate $X_{instr}$ relative to the patient marker. Also as part of process block 118 transformation to volume coordinates is performed with Equation (26) as follows:

$$x_{vol} = T_{reg}^{-1} X_{instr} \quad (26)$$

where $X_{vol}$ is the position of the instrument in the volume coordinate system, aligning with the voxel grid. Thereafter, the transformed instrument positions can be overlaid onto the reconstructed 3D CT volume, providing surgeons with real-time visualization feedback.

By aligning the instrument positions with the reconstructed volume through the shared registration transform $T_{reg}$, surgeons can navigate instruments accurately relative to the patient's anatomy. The consistent use of $T_{reg}$ for both instrument tracking and voxel grid definition ensures that the coordinate systems are synchronized, enhancing the accuracy and reliability of the surgical navigation system.

The projection of voxel coordinates onto the biplanar images using the disclosed transforms bridges the spatial domain (voxel grid) and the projection domain (X-ray images). Such connection facilitates accurate back projection. By projecting voxel coordinates onto the images, the system accurately accounts for the contribution of each voxel to the projections, respecting the imaging geometry defined by the intrinsic and extrinsic parameters, and corrected for distortions. The voxel-wise correspondence between the spatial domain and the image domain provides the deep learning model 65 with structured input data that reflects the true geometry of the imaging system. This connection facilitates patient coordinate alignment. Since the voxel grid is defined using the registration transform derived from the projection vectors, the reconstructed volume inherently aligns with the patient's anatomy and the instrument tracking system, enabling direct navigation without additional transformations.

FIG. 16 is a further conceptual sub-flow diagram of the surgical navigation phase 16 of FIGS. 2A-B in accordance with the disclosure. In particular, the process acts for process blocks 31 and 33 are illustrated in greater detail in FIG. 16 with the described acts illustrated in process blocks 81, 83 and 85 thereof. Specifically, given the input sources of a reconstructed 3D volume, the computed registration transform and output of the optical tracking cameras process, block 81 represents the steps necessary for real-time instrument tracking for both instruments with marker arrays and without markers. Specifically, process block 81 encompasses the acts of detecting any reference markers on the instruments, and, if markers are detected, determining the six degrees of freedom pose of the instrument. If no markers are detected, object recognition software and 3D localization algorithms are utilized to recognize the instrument pose. The output of either of these instrument positions is transformed into the world coordinate system. Process block 83 illustrates the a subprocesses for coordinate transformation, including computing an inverse of the registration transform, transforming the instrument position to volume coordinates and validating that the transformed instrument coordinates are within the bounds of the 3D volume. Such transformations use the same registration transform as used for the 3D volume reconstruction.

Next, the multi-planar reconstruction is utilized to provide real-time display as illustrated by process block 85. In particular, 3D volume renderings from the reconstructed CT volume and the instrument overlay generated in process block 83 are combined to provide multiples views of the patient anatomy including axle, sagittal, coronal, and 3D views updated in real time as illustrated.

The methods described herein may be implemented on a computer 116 using well-known computer processors, memory units, storage devices, computer software, and other components. A high-level block diagram of such a computer is illustrated in FIG. 17. In embodiments, computer 116 comprises display 118, processor 220, I/O interface 222, memories 224 and 226, and network interface 225, all operatively interconnected by bus 223. Network interface 225 operatively connects cameras 114, radiographic image detector 115A, and external memory 227 to the other components of computer 116, as illustrated in FIG. 17. Processor 220 controls the overall operation of the computer 116 by executing software modules or applications comprising computer program instructions 288 which define such operation functionality. The computer program instructions 228 may be stored directly in memory 224 or in an external storage device 227 (e.g., magnetic disk) and loaded into memory 224 when execution of the computer program instructions is desired. Thus, the processes described herein may be defined by the computer program instructions stored in the memory 224 and/or storage 227 and controlled by the processor 220 executing the computer program instructions. ROM memory 226 typically contains computer program instructions comprising the operating system and basic input/output system firmware to provide runtime services for the operating and programs and to perform hardware initialization during power on startup processes.

A radiographic image detector 115A, such as a CT scanner, C-arm CT scanner, or X-ray scanner, or other radiographic image detector, can be connected to the computer 116 via network interface 225 to input image data to the computer 116. It is possible to implement the radiographic image detector 115A and the computer 116 as one device. It is also possible that radiographic image detector 115A and the computer 116 communicate wirelessly through a network infrastructure. In embodiments, the computer 116 can be located remotely with respect to the radiographic image detector 115A and the process described herein can be performed as part of a server or cloud based service. In this case, the process may be performed on a single computer or distributed between multiple networked computers. The computer 116 also includes one or more network interfaces 125 for communicating with other devices via a network. The computer 116 also includes other input/output devices 222 that enable user interaction with the computer 116 (e.g., display, keyboard, mouse, speakers, joystick controllers, etc.). One skilled in the art will recognize that an implementation of an actual computer could contain other components as well, and that FIG. 17 is a high level representation of some of the components of such a computer for illustrative purposes.

In light of the foregoing description, the reader will appreciate the following benefit advantages of the disclosed system and methods. The numerous advantages of the disclosed system and methods include the following. The disclosed system and method address the problem of limited projection data. As disclosed herein, by using deep learning, the limitations of traditional reconstruction methods that require numerous projections over a wide angular range are overcome. The disclosed system and method address the problem of limited pose estimation accuracy. As disclosed herein, integration of optical tracking and camera calibration provides precise pose information needed for accurate reconstruction and instrument tracking. The disclosed system and method address the problem of automatic instrument registration. As disclosed herein, enabling automatic registration enhances the feasibility of minimally invasive procedures, reducing the need for exposing the patient's anatomy. The disclosed system and method address the problem of marker-less instrument tracking. As disclosed herein, utilizing object recognition and 3D localization algorithms, instruments can be tracked without the need for attached reference arrays, simplifying the surgical workflow. The disclosed system and method address the problem of distortion correction. As disclosed herein, correcting non-linear distortions in the X-ray images improves the accuracy of back-projection and reconstruction, especially when using image intensifier systems. The disclosed system and method address the problem of voxel grid alignment. As disclosed, defining the voxel grid using the registration transform ensures that the reconstructed volume is in the patient coordinate system and consistent with the instrument tracking system. This alignment also ensures that the grid points fall within the field of view of the X-ray images when projected, to ensure effective reconstruction. The disclosed system and method address the problem of minimal radiation exposure. As disclosed herein, capturing only two X-ray images reduces patient exposure to radiation compared to traditional CT scanning. The disclosed system and method address the problem of integration of modalities. As disclosed herein, combining optical tracking with radiographic imaging leverages the strengths of both modalities for enhanced imaging capabilities. The disclosed system and method address the problem of enhanced surgical navigation. As disclosed herein, the ability to track surgical instruments within the reconstructed volume provides surgeons with real-time, precise guidance, improving surgical outcomes.

Although the systems and methods disclosed herein have been described with reference to patient anatomy and surgical navigation procedures, their applicability is not limited to the same. Any of the systems and methods disclosed herein may be utilized in other situations, including industrial control, package or baggage handling, or any other environments in which the near real-time position and tracking of objects within a volume is required.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

At various places in the present specification, values are disclosed in groups or in ranges. It is specifically intended that the description includes each and every individual sub-combination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

For purposes of clarity and a concise description, features are described herein as part of the same or separate embodiments, however, it will be appreciated that scope of the concepts may include embodiments having combinations of all or some of the features described herein. Further, terms such as "first," "second," "top," "bottom," "front," "rear," "side," and other are used for reference purposes only and are not meany to be limiting.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to an example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method of synchronizing coordinate systems in a surgical navigation system comprising:
   A) acquiring a pair of biplanar images;
   B) generating a projection vector from each of the biplanar images;
   C) deriving a registration transform function from parameters of the projection vectors;
   D) defining a point of intersection of the projection vectors in a first three-dimensional space as a center of a voxel grid;
   E) back-projecting the voxel grid to create a three-dimensional volume of the biplanar images;
   F) detecting a position of an instrument within a patient coordinate system;
   G) aligning the instrument position with the three-dimensional volume; and
   H) projecting an image of the aligned instrument position overlayed over the three-dimensional volume.

* * * * *